US012648944B2

(12) United States Patent
Moussy et al.

(10) Patent No.: US 12,648,944 B2
(45) Date of Patent: Jun. 9, 2026

(54) MASITINIB FOR THE TREATMENT OF CASTRATE-RESISTANT PROSTATE CANCER

(71) Applicant: AB SCIENCE, Paris (FR)

(72) Inventors: Alain Moussy, Paris (FR); Colin Mansfield, Paris (FR)

(73) Assignee: AB SCIENCE, Paris (FR)

( * ) Notice: Subject to any disclaimer, the term of this patent is extended or adjusted under 35 U.S.C. 154(b) by 596 days.

(21) Appl. No.: 18/040,884

(22) PCT Filed: May 17, 2022

(86) PCT No.: PCT/EP2022/063361
§ 371 (c)(1),
(2) Date: Feb. 7, 2023

(87) PCT Pub. No.: WO2022/243339
PCT Pub. Date: Nov. 24, 2022

(65) Prior Publication Data

US 2023/0321081 A1 Oct. 12, 2023

(30) Foreign Application Priority Data

May 17, 2021 (EP) .................................... 21305643

(51) Int. Cl.
*A61K 31/496* (2006.01)
*A61K 45/06* (2006.01)
*A61P 35/04* (2006.01)

(52) U.S. Cl.
CPC ............ *A61K 31/496* (2013.01); *A61K 45/06* (2013.01); *A61P 35/04* (2018.01)

(58) Field of Classification Search
CPC ........ A61K 31/496; A61K 45/06; A61P 35/04
See application file for complete search history.

(56) References Cited

U.S. PATENT DOCUMENTS

| | | | |
|---|---|---|---|
| 7,423,055 | B2 | 9/2008 | Ciufolini et al. |
| 2017/0196853 | A1 | 7/2017 | Moussy et al. |

FOREIGN PATENT DOCUMENTS

| | | | |
|---|---|---|---|
| EP | 1525200 B1 | 10/2007 | |
| WO | 2008098949 A2 | 8/2008 | |

OTHER PUBLICATIONS

Clinical Trial NCT03761225 (Ab Science, citations from V6 update posted Apr. 6, 2020, henceforth NCT '225) (Year: 2020).*
International Search Report issued on Sep. 21, 2022, in corresponding International Application No. PCT/EP2022/063361, 4 pages.
Crawford et al., "Navigating the evolving therapeutic landscape in advanced prostate cancer", Urologic Oncology: Seminars and Original Investigations, May 2017, vol. 35, pages S1-S13.
Eisenhauer et al., "New response evaluation criteria in solid tumours: revised RECIST guideline (version 1.1)", European Journal of Cancers, Jan. 2009, vol. 45, No. 2, pp. 228-247.
Halabi et al., "Prognostic model for predicting survival in men with hormone-refractory metastatic prostate cancer", Journal of Clinical Oncology, Apr. 1, 2003, vol. 21, No. 7, pp. 1232-1237.
Hofmarcher et al., "Comparator Report on Cancer in Europe 2019 - Disease Burden, Costs and Access to Medicines", IHE Report, 2019, vol. 7, 230 pages.
Kristi, "Masitinib Plus Docetaxel Improves PFS in Metastatic Castration-Resistant Prostate Cancer", Apr. 30, 2021, 12 pages, retrieved from the Internet: URL: https://www.onclive.com/view/masitinib-plus-docetaxel-improves-pfs-in-metastatic-castration-resistant-prostate-cancer.
Oken et al., "Toxicity and response criteria of the Eastern Cooperative Oncology Group", American Journal of Clinical Oncology, Dec. 1982, vol. 5, No. 6, pp. 649-655.
Saad et al., "Guidelines for the management of castrate-resistant prostate cancer", Canadian Urological Association Journal, Dec. 2010, vol. 4, No. 6, pp. 380-384.
Scher et al., "Design and end points of clinical trials for patients with progressive prostate cancer and castrate levels of testosterone: recommendations of the Prostate Cancer Clinical Trials Working Group", NIH Public Access Author Manuscript, Journal of Clinical Oncology, Mar. 1, 2008, vol. 26, No. 7, pp. 1148-1159.
Sonpavde et al., "Serum alkaline phosphatase changes predict survival independent of PSA changes in men with castration-resistant prostate cancer and bone metastasis receiving chemotherapy", Urologic Oncology: Seminars and Original Investigations, Sep. 2012, vol. 30, No. 5, pp. 607-613.
Sung et al., "Global Cancer Statistics 2020: GLOBOCAN Estimates of Incidence and Mortality Worldwide for 36 Cancers in 185 Countries", Ca: A Cancer Journal for Clinicians, May 2021, vol. 71, No. 3, pp. 209-249.
AB Science, "Phase 2B/3 Study Evaluating Masitinib In In Metastatic Castrate-Resistant Prostate Cancer (MCRPC) Met Its Primary Endpoint", Apr. 29, 2021, 3 pages.
AB Science, "Update On Masitinib Phase 3 Study (AB12003) In Metastatic Castrate-Resistant Prostate Cancer (MCRPC) Eligible To Chemotherapy", Mar. 31, 2021, 3 pages.

(Continued)

*Primary Examiner* — Kamal A Saeed
*Assistant Examiner* — Quincy Mckoy
(74) *Attorney, Agent, or Firm* — Maier & Maier, PLLC

(57) ABSTRACT

Masitinib, or a pharmaceutically acceptable salt or solvate thereof, for use in the treatment of metastatic castrate-resistant prostate cancer (mCRPC) in a subject in need thereof. In particular, masitinib, or a pharmaceutically acceptable salt or solvate thereof, for use in the treatment of mCRPC in a subject suffering from early mCRPC associated (i) with alkaline phosphatase (ALP) levels at baseline equal to or lower than 250 IU/L, or (ii) with a Halabi prognosis score (H) at baseline equal to or lower than 33, or (iii) with ALP levels at baseline equal to or lower than 250 IU/L and with a Halabi prognosis score (H) at baseline equal to or lower than 33.

16 Claims, No Drawings

(56) References Cited

OTHER PUBLICATIONS

AB Science, "FDA green-lights U.S. patient enrollment in masitinib Phase 3 study following IND clearance in metastatic castrate-resistant prostate cancer eligible to chemotherapy", Jan. 8, 2020, 2 pages.

"EU Clinical Trials Register", EudraCT No. 2013-000809-23, retrieved from Internet https://www.clinicaltrialsregister.eu/ctr-search/trial/2013-000809-23/GB, Apr. 27, 2021, 6 pages.

ClinicalTrials.gov—NCT03761225—Masitinib Plus Docetaxel in Metastatic Castration-resistant Prostate Cancer—retrieved from Internet https://clinicaltrials.gov/ct2/show/NCT03761225, Apr. 27, 2021, 7 pages.

* cited by examiner

MASITINIB FOR THE TREATMENT OF CASTRATE-RESISTANT PROSTATE CANCER

FIELD

The present invention relates to the treatment of prostate cancer, in particular of castrate-resistant prostate cancer (CRPC).

BACKGROUND

Prostate cancer is one of the most common cancers in men. There were an estimated 1,414,259 new cases of prostate cancer diagnosed worldwide in 2020, representing 7.3% of the estimated total new cancer cases (Sung H et al. C A Cancer J Clin. 2021 May; 71 (3): 209-249. doi: 10.3322/caac.21660). In the United States of America, the incidence rate, based on the 2013-2017 data, was 104.6 new cases per 100,000 men per year (American Cancer Society, 2018-Data sources: North American Association of Central Cancer Registries (NAACCR), 2020). In Europe, the average incidence rate was estimated in 2018 at 151.2 new cases per 100,000 men, with an average death rate estimated the same year at 32.8 per 100,000 (Hofmarcher, T et al. (2019) Comparator Report on Cancer in Europe 2019-Disease Burden, Costs and Access to Medicines. IHE Report 2019:7. IHE: Lund, Sweden).

Prostate cancer is driven by male sex hormones called androgens, including testosterone and dihydrotestosterone (DHT). Hormone therapy, aiming either at decreasing androgen levels or blocking androgen action, can inhibit the growth of prostate cancer. Usually, the first type of hormone therapy administered to treat prostate cancer is the so-called androgen deprivation therapy (ADT), consisting of treatments reducing androgen production by the testicles. ADT thus includes surgical castration (i.e., orchiectomy) and chemical (or medical) castration. Chemical castration may be obtained through the administration of luteinizing hormone-releasing hormone (LHRH) agonists, sometimes called LHRH analogs, or through the administration of LHRH antagonists. Of note, LHRH is also sometimes called gonadotropin-releasing hormone (GnRH) and, accordingly, LHRH agonists (or analogs) are also known as GnRH agonists (or analogs), and LHRH antagonists as GnRH antagonists.

Most prostate cancers eventually stop responding to androgen deprivation therapy and thus become castrate-(or castration-) resistant. Castrate-resistant prostate cancer (CRPC) is defined by disease progression despite androgen deprivation therapy and may present as either a continuous rise in serum prostate-specific antigen (PSA) levels, the progression of pre-existing disease, and/or the appearance of new metastases (Saad et al. Can Urol Assoc J. 2010 December; 4 (6): 380-4). Treatment options then comprise further hormone therapies, such as antiandrogen therapies including androgen receptor blockers and androgen synthesis inhibitors (for example abiraterone), immunotherapy, and chemotherapy, in particular docetaxel or cabazitaxel.

Of note, androgen deprivation therapy is also currently part of the standard of care for metastatic prostate cancer. Although the majority of patients with metastatic prostate cancer initially respond to castration, either surgical or chemical, almost all patients with metastatic prostate cancer will also eventually develop castration resistance. These patients are then suffering from metastatic castrate-(or castration-) resistant prostate cancer (mCRPC). Treatment options for mCRPC primarily aim at prolonging life and improving quality of life. However, median survival for patients with mCRPC ranges from approximately 15 to 36 months in recent studies, and 5-year survival is only 28% (Crawford et al. Urol Oncol. 2017 May; 35S: S1-S13). The reported impact of currently approved treatments for mCRPC remains modest.

Therefore, there is still a need for effective treatment for metastatic castrate-(or castration-) resistant prostate cancer (mCRPC). In particular, it may be helpful to identify the mCRPC patients most likely to benefit from treatment.

The present invention thus relates to masitinib, or a pharmaceutically acceptable salt or solvate thereof, for use in the treatment of metastatic castrate-resistant prostate cancer (mCRPC) in a subject in need thereof, in particular in a subject most likely to benefit from the administration of masitinib, or a pharmaceutically acceptable salt or solvate thereof, such as a subject having alkaline phosphatase levels at baseline equal to or lower than 250 IU/L and/or with a Halabi prognosis score (H) at baseline equal to or lower than 33.

SUMMARY

The present invention relates to masitinib, or a pharmaceutically acceptable salt or solvate thereof, for use in the treatment of metastatic castrate-resistant prostate cancer (mCRPC) in a subject in need therefore, wherein said subject suffers from early mCRPC associated (i) with alkaline phosphatase (ALP) levels at baseline equal to or lower than 250 IU/L, or (ii) with a Halabi prognosis score (H) at baseline equal to or lower than 33, or (iii) with ALP levels at baseline equal to or lower than 250 IU/L and with a Halabi prognosis score (H) at baseline equal to or lower than 33.

In one embodiment, said subject has ALP levels at baseline equal to or lower than 240, 230, 220, 210, 200, 190, 180, 170, 160, 150, 140, 130, 120, 110, or 100 IU/L. In one embodiment, said subject has ALP levels at baseline equal to or lower than 200 IU/L. In one embodiment, said subject has ALP levels at baseline equal to or lower than 150 IU/L. In one embodiment, said subject has ALP levels at baseline equal to or lower than 100 IU/L.

In one embodiment, said subject has a Halabi prognosis score (H) at baseline equal to or lower than 32, 31, 30, 29, 28, 27, 26, 25, 24, 23, 22, 21, 20, 19, 18, 17, 16, or 15. In one embodiment, said subject has a Halabi prognosis score (H) at baseline equal to or lower than 22.

In one embodiment, said subject received hormone therapy selected from the group consisting of luteinizing hormone-releasing hormone (LHRH) agonists (also known as gonadotropin-releasing hormone (GnRH) agonists), LHRH antagonists (also known as GnRH antagonists), and abiraterone.

In one embodiment, the pharmaceutically acceptable salt of masitinib is masitinib mesilate.

In one embodiment, masitinib, or a pharmaceutically acceptable salt or solvate thereof, is for administration at a dose ranging from about 1 to about 12 mg/kg/day (mg per kilo body weight per day), preferably at a dose ranging from about 3 to about 6 mg/kg/day. In one embodiment, masitinib, or a pharmaceutically acceptable salt or solvate thereof, is for administration at a dose of about 6 mg/kg/day.

In one embodiment, masitinib, or a pharmaceutically acceptable salt or solvate thereof, is for oral administration. In one embodiment, masitinib, or a pharmaceutically acceptable salt or solvate thereof, is for administration in two daily intakes.

In one embodiment, masitinib, or a pharmaceutically acceptable salt or solvate thereof, is for administration with at least one further pharmaceutically active agent. In one embodiment, said at least one further pharmaceutically active agent is selected from chemotherapeutic agents and corticoids.

In the present invention, the following terms have the following meanings:

"About" preceding a figure encompasses plus or minus 10%, or less, of the value of said figure. It is to be understood that the value to which the term "about" refers is itself also specifically, and preferably, disclosed.

"ALP" refers to alkaline phosphatase. ALP is a membrane-bound glycoprotein which catalyzes the hydrolysis of organic phosphate esters present in the extracellular space. ALP is ubiquitous and can be found in a number of different tissues (such as, for example, placenta, intestine, kidney, bone, and liver) from which it is released in the blood. As used herein, "ALP levels" refer to ALP levels in the blood, in particular in the serum.

"Baseline" as used herein refers to the time preceding the start of treatment with a 2-aminoarylthiazole derivative, in particular masitinib, or a pharmaceutically acceptable salt or solvate thereof, as described herein. For example, for a given subject, the ALP levels at baseline are the ALP levels prior to the administration to the subject of a 2-aminoarylthiazole derivative, in particular masitinib, or a pharmaceutically acceptable salt or solvate thereof, as described herein. Accordingly, for a given subject, the Halabi prognosis score (H) at baseline is the Halabi prognosis score (H) prior to the administration to the subject of a 2-aminoarylthiazole derivative, in particular masitinib, or a pharmaceutically acceptable salt or solvate thereof, as described herein.

"Pharmaceutically acceptable excipient" or "pharmaceutically acceptable carrier" refers to an excipient or carrier that does not produce an adverse, allergic or other untoward reaction when administered to a subject. It includes any and all solvents, such as, for example, dispersion media, coatings, antibacterial and antifungal agents, isotonic and absorption delaying agents. A pharmaceutically acceptable excipient or carrier refers to a non-toxic solid, semi-solid or liquid filler, diluent, encapsulating material or formulation auxiliary of any type. For human administration, preparations should meet sterility, pyrogenicity, general safety and purity standards as required by the regulatory offices such as the FDA (U.S. food and drug administration) or EMA (European medicines agency).

"Subject" refers to a mammal, preferably a human. In one embodiment, the mammal is selected from cats, dogs, cows, pigs, horses, monkeys, apes and humans. In one embodiment, the mammal is selected from cats, dogs and humans. In one embodiment, the subject is a primate. In one embodiment, the subject is a human. In one embodiment, the subject may be a "patient", i.e., a mammal, preferably a human, who/which is awaiting the receipt of, or is receiving medical care or was/is/will be the object of a medical procedure, or is monitored for the development of prostate cancer. In one embodiment, a "subject in need of treatment" is a subject who is awaiting the receipt of, or is receiving medical care, or was/is/will be the object of a medical procedure, or is monitored for the development of prostate cancer, in particular metastatic castrate-resistant prostate cancer (mCRPC).

"Therapeutically effective amount" or "therapeutically effective dose" refers to the amount or concentration of a 2-aminoarylthiazole derivative as described herein, in particular masitinib, or a pharmaceutically acceptable salt or solvate thereof, that is aimed at, without causing significant negative or adverse side effects to the subject in need of treatment, bringing about at least one of the following: (1) slowing down or stopping the progression, aggravation, or deterioration of one or more symptom(s) of castrate-resistant prostate cancer (CRPC), in particular mCRPC, and notably prolonging survival of the subject, in particular progression-free survival; (2) bringing about ameliorations of the symptoms of CRPC, in particular mCRPC; (3) reducing the severity or incidence of CRPC, in particular mCRPC; (4) decreasing prostate specific antigen (PSA) levels (e.g., by at least 30% from baseline PSA levels), (5) curing CRPC, in particular mCRPC, (6) increasing quality of life or (7) decreasing pain intensity.

"Treating" or "Treatment" refers to a therapeutic treatment, to a prophylactic (or preventative) treatment, or to both a therapeutic treatment and a prophylactic (or preventative) treatment, wherein the object is to prevent, reduce, or slow down (lessen) one or more of the symptom(s) or manifestation(s) of castrate-resistant prostate cancer (CRPC), in particular of mCRPC. In one embodiment, a subject is successfully "treated" for CRPC, in particular mCRPC, if, after receiving a therapeutic amount of a 2-aminoarylthiazole derivative as described herein, in particular masitinib, or a pharmaceutically acceptable salt or solvate thereof, the subject shows observable and/or measurable reduction in the number or percent of cancer cells or metastatic cells; and/or if the subject shows relief to some extent of one or more of the symptoms associated with CRPC, in particular of mCRPC; reduced PSA levels; reduced pain; reduced morbidity and mortality; and/or improvement in quality of life issues. In one embodiment, a subject is successfully "treated" for CRPC, in particular mCRPC, if, after receiving a therapeutic amount of a 2-aminoarylthiazole derivative as described herein, in particular masitinib, or a pharmaceutically acceptable salt or solvate thereof, the subject benefits from an extended survival, in particular of an extended progression-free survival. The above parameters for assessing successful treatment and improvement in the disease are readily measurable by routine procedures familiar to a physician.

DETAILED DESCRIPTION

The present invention relates to a 2-aminoarylthiazole derivative as described herein, in particular masitinib, or a pharmaceutically acceptable salt or solvate thereof, for use in the treatment of prostate cancer in a subject in need thereof as defined hereinafter.

According to one embodiment, prostate cancer is castrate-resistant prostate cancer also known as castration-resistant prostate cancer (CRPC).

According to one embodiment, prostate cancer is metastatic prostate cancer, in particular metastatic castrate-resistant prostate cancer (mCRPC).

According to one embodiment, the subject in need of treatment has alkaline phosphatase (ALP) levels at baseline equal to or lower than 250, 240, 230, 220, 210, 200, 190, 180, 170, 160, 150, 140, 130, 120, 110, or 100 IU/L. Thus, according to one embodiment, prior to treatment with a 2-aminoarylthiazole derivative as described herein, in particular masitinib, or a pharmaceutically acceptable salt or solvate thereof, the subject has ALP levels equal to or lower than 250, 240, 230, 220, 210, 200, 190, 180, 170, 160, 150, 140, 130, 120, 110, or 100 IU/L.

Methods to measure ALP levels are well-known to one skilled in the art and include, for example, the alkaline phosphatase isoenzyme blood test. ALP levels are expressed in IU/L (international units per liter) or in microkatals per liter (μkat/L). The normal range of ALP levels in human healthy adults is generally considered to be about 44 to about 147 IU/L. ALP levels are often elevated in subjects suffering from prostate cancer (including CRPC), in particular in subjects suffering from metastatic prostate cancer (including mCRPC). ALP levels can thus reach up to about 1000-3000 IU/L in human subjects suffering from metastatic prostate cancer (including mCRPC).

In one embodiment, the subject in need of treatment has ALP levels at baseline equal to or lower than 250 IU/L. In one embodiment, the subject in need of treatment has ALP levels at baseline equal to or lower than 200 IU/L. In one embodiment, the subject in need of treatment has ALP levels at baseline equal to or lower than 150 IU/L. In one embodiment, the subject in need of treatment has ALP levels at baseline equal to or lower than 100 IU/L.

According to one embodiment, the subject in need of treatment has a Halabi prognosis score (H) at baseline equal to or lower than 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, or 15. Thus, according to one embodiment, prior to treatment with a 2-aminoarylthiazole derivative as described herein, in particular masitinib, or a pharmaceutically acceptable salt or solvate thereof, the subject has a Halabi prognosis score (H) equal to or lower than 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, or 15.

As used herein, the so-called Halabi prognosis score (H) is based on the method described by Halabi et al. (J Clin Oncol. 2003 Apr. 1; 21 (7): 1232-7), which is incorporated herein by reference.

More specifically, the Halabi prognosis score (H) as defined herein is obtained with a mathematic formula used to model and estimate patient survival, which is based on the measurement of visceral disease (yes or no, the value of this parameter being equal to 1 if the subject is affected with visceral disease, and 0 if he is not), initial Gleason score (the value being equal to 1 if the Gleason score measured for the subject ranges from 8 to 10, and 0 if the Gleason score is inferior to 8), ECOG (Eastern Cooperative Oncology Group) performance status (ranging from 0 to 2), prostate specific antigen (PSA) levels (PSA, measured in ng/mL), lactic acid dehydrogenase (LDH) levels (LDH, measured in IU/L), alkaline phosphatase (ALP) levels (ALP or AP, measured in IU/L) and hemoglobin (HB, measured in g/dL).

In one embodiment, the Halabi prognosis score (H) (i.e., survival estimate) is calculated using the following formula:

$$H=[0.392\times(2\text{ if ECOG}=2,\ 1\text{ if ECOG}=1,\ 0\text{ if ECOG}=0)]+[0.335\times(1\text{ if Gleason Score in }[8\text{-}10],\ 0\text{ if Gleason Score}<8)]+[\exp(0.312\times\log(LDH)+0.211\times\log(AP)+0.093\times\log(PSA))]+[0.161\times(1\text{ if presence of visceral disease, else }0)]-[0.082\times HB].$$

In the mathematic formula hereinabove, ECOG is for Eastern Cooperative Oncology Group status and corresponds to a scale published in 1982 (Oken et al., Am J Clin Oncol. 1982; 5:649-655) and describing a patient's level of functioning in terms of their ability to care for themself, daily activity, and physical ability (walking, working, etc.). The ECOG performance status comprises 6 grades, from 0 (fully active, able to carry on all pre-disease performance without restriction) to 5 (dead). Grade 1 corresponds to a patient restricted in physically strenuous activity but ambulatory and able to carry out work of a light or sedentary nature, e.g., light house work, office work; grade 2 corresponds to a patient ambulatory and capable of all selfcare but unable to carry out any work activities, up and about more than 50% of waking hours; grade 3 corresponds to a patient capable of only limited selfcare, confined to bed or chair more than 50% of waking hours; and grade 4 corresponds to a completely disabled patient, who cannot carry on any selfcare, totally confined to bed or chair. In the present invention, the ECOG performance status of the subject ranges from 0 to 2.

In one embodiment, the subject has an ECOG performance status of 0 or 1, and the Halabi prognosis score (H) (i.e., survival estimate) may be calculated using the following formula:

$$H=[0.392\times(1\text{ if ECOG}=1,\ 0\text{ if ECOG}=0)]+[0.335\times(1\text{ if Gleason Score in }[8\text{-}10],\ 0\text{ if Gleason Score}<8)]+[\exp(0.312\times\log(LDH)+0.211\times\log(AP)+0.093\times\log(PSA))]+[0.161\times(1\text{ if presence of Visceral Disease, else }0)]-[0.082\times HB].$$

The Gleason score is a prognostic score for prostate cancer patients, obtained from prostate biopsy samples based on the microscopic appearance. The score ranges from 2 to 10, with higher numbers indicating greater risks and higher mortality. For measuring the score, two patterns are measured, the first one based on the dominant or most common cell morphology (scored 1-5) and the second one based on the non-dominant cell pattern (also scored 1-5). The two patterns are thus combined to obtain a score ranging from 2 to 10. Gleason's patterns are the following: 1—small, uniform glands, 2—more stroma between glands, 3—distinctly infiltrative margins, 4—irregular masses of neoplastic glands, and 5—only occasional gland formation.

Visceral disease is a clinical manifestation of metastatic CRPC, corresponding to the presence of metastasis, predominantly in the lung and liver.

Methods for measuring lactic acid dehydrogenase (LDH) levels, alkaline phosphatase (ALP or AP) levels, prostate specific antigen (PSA) levels and hemoglobin (HB) levels are well-known to the skilled artisan and commonly implemented in clinical laboratories.

In one embodiment, the subject in need of treatment has a Halabi prognosis score (H) at baseline equal to or lower than 33. In one embodiment, the subject in need of treatment has a Halabi prognosis score (H) at baseline equal to or lower than 27. In one embodiment, the subject in need of treatment has a Halabi prognosis score (H) at baseline equal to or lower than 22. In one embodiment, the subject in need of treatment has a Halabi prognosis score (H) at baseline equal to or lower than 21. In one embodiment, the subject in need of treatment has a Halabi prognosis score (H) at baseline equal to or lower than 19. In one embodiment, the subject in need of treatment has a Halabi prognosis score (H) at baseline equal to or lower than 18. In one embodiment, the subject in need of treatment has a Halabi prognosis score (H) at baseline equal to or lower than 17. In one embodiment, the subject in need of treatment has a Halabi prognosis score (H) at baseline equal to or lower than 16. In one embodiment, the subject in need of treatment has a Halabi prognosis score (H) at baseline equal to or lower than 15.

According to one embodiment, the subject in need of treatment was previously treated by castration treatment, corresponding to the reduction of available androgen, testosterone or dihydrotestosterone (DHT), by chemical or surgical means.

According to one embodiment, the subject in need of treatment received hormone therapy selected from the group consisting of luteinizing hormone-releasing hormone (LHRH) agonists (also known as gonadotropin-releasing hormone (GnRH) agonists), LHRH antagonists (also known as GnRH antagonists), and abiraterone. Thus, according to one embodiment, prior to treatment with a 2-aminoarylthiazole derivative as described herein, in particular masitinib, or a pharmaceutically acceptable salt or solvate thereof, the subject received hormone therapy selected from the group consisting of LHRH agonists (also known as GnRH agonists), LHRH antagonists (also known as GnRH antagonists), and abiraterone. In one embodiment, the subject in need of treatment previously received LHRH agonists (also known as GnRH agonists). Examples of LHRH agonists include, but are not limited to, leuprolide, goserelin, triptorelin and histrelin. In one embodiment, the subject in need of treatment previously received LHRH antagonists (also known as GnRH antagonists). Examples of LHRH antagonists include, but are not limited to, degarelix and relugolix. In one embodiment, the subject in need of treatment previously received abiraterone. In one embodiment, the subject was previously treated by surgical castration.

According to one embodiment, the subject in need of treatment has ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, or 15.

In one embodiment, the subject in need of treatment has ALP levels at baseline equal to or lower than 250 IU/L, and a Halabi prognosis score (H) at baseline equal to or lower than 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, or 15. In one embodiment, the subject in need of treatment has ALP levels at baseline equal to or lower than 200 IU/L, and a Halabi prognosis score (H) at baseline equal to or lower than 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, or 15. In one embodiment, the subject in need of treatment has ALP levels at baseline equal to or lower than 150 IU/L, and a Halabi prognosis score (H) at baseline equal to or lower than 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, or 15. In one embodiment, the subject in need of treatment has ALP levels at baseline equal to or lower than 100 IU/L, and a Halabi prognosis score (H) at baseline equal to or lower than 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, or 15.

In one embodiment, the subject in need of treatment has ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 33. In one embodiment, the subject in need of treatment has ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 27. In one embodiment, the subject in need of treatment has ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 22. In one embodiment, the subject in need of treatment has ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 21. In one embodiment, the subject in need of treatment has ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 20. In one embodiment, the subject in need of treatment has ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 19. In one embodiment, the subject in need of treatment has ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 18. In one embodiment, the subject in need of treatment has ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 17. In one embodiment, the subject in need of treatment has ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 16. In one embodiment, the subject in need of treatment has ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 15.

According to one embodiment, the subject in need of treatment has ALP levels at baseline equal to or lower than 250, 240, 230, 220, 210, 200, 190, 180, 170, 160, 150, 140, 130, 120, 110, or 100 IU/L, and received hormone therapy selected from the group consisting of luteinizing hormone-releasing hormone (LHRH) agonists (also known as gonadotropin-releasing hormone (GnRH) agonists), LHRH antagonists (also known as GnRH antagonists), and abiraterone.

In one embodiment, the subject in need of treatment has ALP levels at baseline equal to or lower than 250, 200, 150, or 100 IU/L, and received hormone therapy selected from the group consisting of LHRH agonists (also known as GnRH agonists), LHRH antagonists (also known as GnRH antagonists), and abiraterone.

According to one embodiment, the subject in need of treatment has a Halabi prognosis score (H) at baseline equal to or lower than 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, or 15, and received hormone therapy selected from the group consisting of LHRH agonists (also known as GnRH agonists), LHRH antagonists (also known as GnRH antagonists), and abiraterone.

In one embodiment, the subject in need of treatment has a Halabi prognosis score (H) at baseline equal to or lower than 33, 27, 22, 21, 20, 19, 18, 17, 16, or 15, and received hormone therapy selected from the group consisting of LHRH agonists (also known as GnRH agonists), LHRH antagonists (also known as GnRH antagonists), and abiraterone.

According to one embodiment, the subject in need of treatment has ALP levels at baseline equal to or lower than 250, 240, 230, 220, 210, 200, 190, 180, 170, 160, 150, 140, 130, 120, 110, or 100 IU/L; and a Halabi prognosis score (H) at baseline equal to or lower than 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, or 15; and received hormone therapy selected from the group consisting of LHRH agonists (also known as GnRH agonists), LHRH antagonists (also known as GnRH antagonists), and abiraterone.

In one embodiment, the subject in need of treatment has ALP levels at baseline equal to or lower than 250 IU/L, and a Halabi prognosis score (H) at baseline equal to or lower than 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, or 15; and received hormone therapy selected from the group consisting of LHRH agonists (also known as GnRH agonists), LHRH antagonists (also known as GnRH antagonists), and abiraterone. In one embodiment, the subject in need of treatment has ALP levels at baseline equal to or lower than 200 IU/L, and a Halabi prognosis score (H) at baseline equal to or lower than 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, or 15; and received hormone therapy selected from the group consisting of LHRH agonists (also known as GnRH agonists), LHRH antagonists (also known as GnRH antagonists), and abiraterone. In one embodiment, the subject in need of treatment has ALP levels at baseline equal to or lower than 150 IU/L, and a Halabi prognosis score (H) at baseline equal to or lower than 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, or 15; and received hormone therapy selected from the group consisting of LHRH agonists (also known as GnRH agonists), LHRH antagonists (also known as GnRH antagonists), and abiraterone. In one embodiment, the subject in need of treatment has ALP levels at baseline equal to or lower than 100 IU/L, and a Halabi prognosis score (H) at baseline equal to or lower than 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, or 15; and received hormone therapy selected from the group consisting of LHRH agonists (also known as GnRH agonists), LHRH antagonists (also known as GnRH antagonists), and abiraterone.

In one embodiment, the subject in need of treatment has ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 33; and received hormone therapy selected from the group consisting of LHRH agonists (also known as GnRH agonists), LHRH antagonists (also known as GnRH antagonists), and abiraterone.

In one embodiment, the subject in need of treatment has ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 27; and received hormone therapy selected from the group consisting of LHRH agonists (also known as GnRH agonists), LHRH antagonists (also known as GnRH antagonists), and abiraterone.

In one embodiment, the subject in need of treatment has ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 22; and received hormone therapy selected from the group consisting of LHRH agonists (also known as GnRH agonists), LHRH antagonists (also known as GnRH antagonists), and abiraterone.

In one embodiment, the subject in need of treatment has ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 21; and received hormone therapy selected from the group consisting of LHRH agonists (also known as GnRH) agonists, LHRH antagonists (also known as GnRH antagonists), and abiraterone.

In one embodiment, the subject in need of treatment has ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 20; and received hormone therapy selected from the group consisting of LHRH agonists (also known as GnRH agonists), LHRH antagonists (also known as GnRH antagonists), and abiraterone.

In one embodiment, the subject in need of treatment has ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 19; and received hormone therapy selected from the group consisting of LHRH agonists (also known as GnRH agonists), LHRH antagonists (also known as GnRH antagonists), and abiraterone.

In one embodiment, the subject in need of treatment has ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 18; and received hormone therapy selected from the group consisting of LHRH agonists (also known as GnRH agonists), LHRH antagonists (also known as GnRH antagonists), and abiraterone.

In one embodiment, the subject in need of treatment has ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 17; and received hormone therapy selected from the group consisting of LHRH agonists (also known as GnRH agonists), LHRH antagonists (also known as GnRH antagonists), and abiraterone.

In one embodiment, the subject in need of treatment has ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 16; and received hormone therapy selected from the group consisting of LHRH agonists (also known as GnRH agonists), LHRH antagonists (also known as GnRH antagonists), and abiraterone.

In one embodiment, the subject in need of treatment has ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 15; and received hormone therapy selected from the group consisting of LHRH agonists (also known as GnRH agonists), LHRH antagonists (also known as GnRH antagonists), and abiraterone.

According to one embodiment, the subject in need of treatment suffers from early metastatic castrate-resistant prostate cancer (mCRPC) associated with ALP levels at baseline equal to or lower than 250, 240, 230, 220, 210, 200, 190, 180, 170, 160, 150, 140, 130, 120, 110, or 100 IU/L, and/or with a Halabi prognosis score (H) at baseline equal to or lower than 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, or 15. Thus, according to one embodiment, the subject in need of treatment suffers from early mCRPC associated (i) with ALP levels at baseline equal to or lower than 250, 240, 230, 220, 210, 200, 190, 180, 170, 160, 150, 140, 130, 120, 110, or 100 IU/L, or (ii) with a Halabi prognosis score (H) at baseline equal to or lower than 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, or 15, or (iii) with ALP levels at baseline equal to or lower than 250, 240, 230, 220, 210, 200, 190, 180, 170, 160, 150, 140, 130, 120, 110, or 100 IU/L and with a Halabi prognosis score (H) at baseline equal to or lower than 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, or 15, In one embodiment, the subject in need of treatment suffers from mCRPC associated with ALP levels at baseline equal to or lower than 250, 240, 230, 220, 210, 200, 190, 180, 170, 160, 150, 140, 130, 120, 110, or 100 IU/L or with a Halabi prognosis score (H) at baseline equal to or lower than 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, or 15.

In one embodiment, the subject in need of treatment suffers from early mCRPC associated with ALP levels at baseline equal to or lower than 250, 240, 230, 220, 210, 200, 190, 180, 170, 160, 150, 140, 130, 120, 110, or 100 IU/L and with a Halabi prognosis score (H) at baseline equal to or lower than 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, or 15.

In one embodiment, the subject in need of treatment suffers from early mCRPC associated with ALP levels at baseline equal to or lower than 250 IU/L and/or with a Halabi prognosis score (H) at baseline equal to or lower than 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, or 15. In one embodiment, the subject in need of treatment suffers from early mCRPC associated with ALP levels at baseline equal to or lower than 200 IU/L and/or with a Halabi prognosis score (H) at baseline equal to or lower than 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, or 15. In one embodiment, the subject in need of treatment suffers from early mCRPC associated with ALP levels at baseline equal to or lower than 150 IU/L and/or with a Halabi prognosis score (H) at baseline equal to or lower than 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, or 15. In one embodiment, the subject in need of treatment suffers from early mCRPC associated with ALP levels at baseline equal to or lower than 100 IU/L and/or with a Halabi prognosis score (H) at baseline equal to or lower than 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, or 15.

In one embodiment, the subject in need of treatment suffers from early mCRPC associated with ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 33. In one embodiment, the subject in need of treatment suffers from early mCRPC associated with ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 27. In one embodiment, the subject in need of treatment suffers from early mCRPC associated with ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 22. In one embodiment, the subject in need of treatment suffers from early mCRPC associated with ALP levels at baseline equal to or lower than 250, 240, 230, 220, 210, 200, 190, 180, 170, 160, 150, 140, 130, 120, 110, or 100 IU/L, and a Halabi prognosis score (H) baseline equal to or lower than 21. In one embodiment, the subject in need of treatment suffers from early mCRPC associated with ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 20. In one embodiment, the subject in need of treatment suffers from early mCRPC associated with ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 19. In one embodiment, the subject in need of treatment suffers from early mCRPC associated with ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 18. In one embodiment, the subject in need of treatment suffers from early mCRPC associated with ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 17. In one embodiment, the subject in need of treatment suffers from early mCRPC associated with ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 16. In one embodiment, the subject in need of treatment suffers from early mCRPC associated with ALP levels at baseline equal to or lower than 250, 240, 230, 220, 210, 200, 190, 180, 170, 160, 150, 140, 130, 120, 110, or 100 IU/L, and a Halabi prognosis score (H) at baseline equal to or lower than 15.

According to one embodiment, the subject in need of treatment suffers from early mCRPC as defined hereinabove and received (preferably before the initiation of the treatment with a 2-aminoarylthiazole derivative as described herein) hormone therapy selected from the group consisting of luteinizing hormone-releasing hormone (LHRH) agonists (also known as gonadotropin-releasing hormone (GnRH) agonists), LHRH antagonists (also known as GnRH antagonists), and abiraterone.

In one embodiment, the subject in need of treatment is an adult. According to the present invention, an adult is a subject above the age of 18, 19, 20, or 21 years. In one embodiment, the subject in need of treatment is older than 20, 25, or 30 years. According to one embodiment, the subject in need of treatment is a child. According to the present invention, a child is a subject below the age of 21, 20, 19, or 18 years.

In one embodiment, the subject in need of treatment has an ECOG performance status of 0 or 1. In another embodiment, the subject in need of treatment has an ECOG performance status of 2.

In one embodiment, the subject is receiving androgen deprivation therapy selected from the group consisting of luteinizing hormone-releasing hormone (LHRH) agonists (also known as gonadotropin-releasing hormone (GnRH) agonists) and LHRH antagonists (also known as GnRH antagonists).

As used herein, a 2-aminoarylthiazole derivative refers to a compound characterized by the presence of a thiazolyl group substituted on position 2 (i.e., between the heterocyclic nitrogen and sulfur atoms) by a secondary or tertiary amine, wherein the nitrogen atom of the amine is substituted by at least one aryl group.

According to one embodiment, the aryl group is substituted by an arylamide group (i.e., NH CO aryl).

In one embodiment, the 2-aminoarylthiazole derivative of the invention has the following formula (I):

(I)

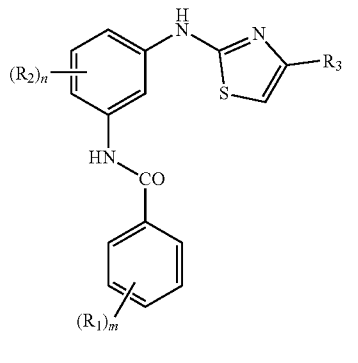

wherein:

$R_1$ and $R_2$ are selected independently from hydrogen, halogen, ($C_1$-$C_{10}$) alkyl, ($C_3$-$C_{10}$) cycloalkyl group, trifluoromethyl, alkoxy, cyano, dialkylamino, a solubilizing group, and ($C_1$-$C_{10}$) alkyl substituted by a solubilizing group;

m is 0-5;

n is 0-4;

$R_3$ is one of the following:

(i) an aryl group (such as phenyl), the aryl group being optionally substituted by one or more substituents such as halogen, ($C_1$-$C_{10}$) alkyl group, trifluoromethyl, cyano and alkoxy;

(ii) a heteroaryl group (such as 2, 3, or 4-pyridyl group), the heteroaryl group being optionally substituted by one or more substituents such as halogen, ($C_1$-$C_{10}$) alkyl group, trifluoromethyl and alkoxy;

(iii) a five-membered ring aromatic heterocyclic group (such as, for example, 2-thienyl, 3-thienyl, 2-thiazolyl, 4-thiazolyl, 5-thiazolyl), the aromatic heterocyclic group being optionally substituted by one or more substituents such as halogen, ($C_1$-$C_{10}$) alkyl group, trifluoromethyl, and alkoxy.

Thus, in one embodiment, the 2-aminoarylthiazole derivative of the invention or a pharmaceutically acceptable salt or solvate thereof is a 2-aminoarylthiazole derivative of formula (I) or a pharmaceutically acceptable salt or solvate thereof.

In one embodiment, the 2-aminoarylthiazole derivative of the invention has the following formula (II):

(II)

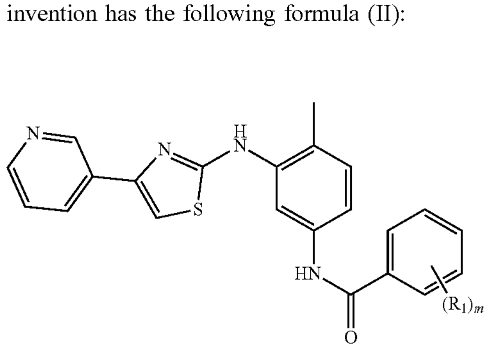

wherein:

$R_1$ is selected independently from hydrogen, halogen, ($C_1$-$C_{10}$) alkyl, ($C_3$-$C_{10}$) cycloalkyl group, trifluoromethyl, alkoxy, amino, alkylamino, dialkylamino, a solubilizing group, and ($C_1$-$C_{10}$) alkyl substituted by a solubilizing group; and m is 0-5.

In one embodiment, $R_1$ of formula (II) is a solubilizing group. In one embodiment, $R_1$ of formula (II) is ($C_1$-$C_{10}$) alkyl substituted by a solubilizing group.

In one embodiment, $R_1$ of formula (II) is ($C_1$-$C_{10}$) alkyl-($C_2$-$C_{11}$) heterocycloalkyl-($C_1$-$C_{10}$) alkyl-. In one embodiment, $R_1$ of formula (II) is ($C_1$-$C_4$) alkyl-($C_2$-$C_{11}$) heterocycloalkyl-($C_1$-$C_{10}$) alkyl-, preferably ($C_1$-$C_2$) alkyl-($C_2$-$C_{11}$) heterocycloalkyl-($C_1$-$C_{10}$) alkyl-. In one embodiment, $R_1$ of formula (II) is ($C_1$-$C_{10}$) alkyl-($C_2$-$C_{11}$) heterocycloalkyl-($C_1$-$C_4$) alkyl-, preferably ($C_1$-$C_{10}$) alkyl-($C_2$-$C_{11}$) heterocycloalkyl-($C_1$-$C_2$) alkyl-. In one embodiment, $R_1$ of formula (II) is ($C_1$-$C_{10}$) alkyl-($C_2$-$C_6$) heterocycloalkyl-($C_1$-$C_{10}$) alkyl-, preferably ($C_1$-$C_{10}$) alkyl-($C_4$) heterocycloalkyl-($C_1$-$C_{10}$) alkyl-. In one embodiment, $R_1$ of formula (II) is ($C_1$-$C_4$) alkyl-($C_2$-$C_6$) heterocycloalkyl-($C_1$-$C_4$) alkyl-, preferably ($C_1$-$C_2$) alkyl-($C_4$) heterocycloalkyl-($C_1$-$C_2$) alkyl-. In one embodiment, $R_1$ of formula (II) is ($C_1$-$C_4$) alkyl-piperazinyl-($C_1$-$C_4$) alkyl-, preferably ($C_1$-$C_2$) alkyl-piperazinyl-($C_1$-$C_2$) alkyl-. In one embodiment, $R_1$ of formula (II) is methylpiperazinyl-($C_1$-$C_2$) alkyl-, preferably methylpiperazinyl-methyl-, more preferably 4-methylpiperazinyl-methyl-.

Thus, in one embodiment, the 2-aminoarylthiazole derivative of the invention or a pharmaceutically acceptable salt or solvate thereof is a 2-aminoarylthiazole derivative of formula (II) as described above or a pharmaceutically acceptable salt or solvate thereof.

As used herein, the term "aryl group" refers to a polyunsaturated, aromatic hydrocarbyl group having a single aromatic ring (i.e., phenyl) or multiple aromatic rings fused together (e.g., naphtyl) or linked covalently, typically containing 5 to 12 atoms; preferably 6 to 10, wherein at least one ring is aromatic. The aromatic ring may optionally include one to two additional rings (either cycloalkyl, heterocyclyl or heteroaryl) fused thereto. Aryl is also intended to include the partially hydrogenated derivatives of the carbocyclic systems enumerated herein. Examples of suitable aryl groups include, without being limited to, phenyl, tolyl, anthracenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or more substituents. In one embodiment, the aryl group is a monocyclic ring, wherein the ring comprises 6 carbon atoms, referred to herein as "($C_6$) aryl".

As used herein, the term "alkyl group" refers to a saturated straight chain or branched non-cyclic hydrocarbon having from 1 to 10 carbon atoms, preferably from 1 to 6 carbon atoms. Representative saturated straight chain alkyls include, without being limited to, methyl, ethyl, n-propyl, n-butyl, n-pentyl, n-hexyl, n-heptyl, n-octyl, n-nonyl and n-decyl. Saturated branched alkyls include, without being limited to, isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl. Alkyl groups included in compounds of the present invention may be optionally substituted with one or more substituents.

As used herein, the term "alkoxy" refers to an alkyl group which is attached to another moiety by an oxygen atom. Examples of alkoxy groups include, without being limited to, methoxy, isopropoxy, ethoxy, tert-butoxy. Alkoxy groups may be optionally substituted with one or more substituents.

As used herein, the term "cycloalkyl" refers to a saturated cyclic alkyl radical having from 3 to 10 carbon atoms. Representative cycloalkyls include cyclopropyl, 1-methylcyclopropyl, cyclobutyl, cyclopentyl, cyclohexyl, cycloheptyl, cyclooctyl, cyclononyl, and cyclodecyl. Cycloalkyl groups can be optionally substituted with one or more substituents.

As used herein, the term "halogen" refers to —F, —Cl, —Br or —I.

As used herein, the term "heteroaryl" refers to a monocyclic or polycyclic heteroaromatic ring comprising carbon atom ring members and one or more heteroatom ring members (such as, for example, oxygen, sulfur or nitrogen). Typically, a heteroaryl group has from 1 to about 5 heteroatom ring members and from 1 to about 14 carbon atom ring members. Representative heteroaryl groups include, without being limited to, pyridyl, 1-oxo-pyridyl, furanyl, benzo[1,3]dioxolyl, benzo[1,4]dioxinyl, thienyl, pyrrolyl, oxazolyl, imidazolyl, thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo[1,2-a]pyridyl, and benzo (b) thienyl. A heteroatom may be substituted with a protecting group known to those of ordinary skill in the art, for example, the hydrogen on a nitrogen may be substituted with a tert-butoxycarbonyl group. Heteroaryl groups may be optionally substituted with one or more substituents. In addition, nitrogen or sulfur heteroatom ring members may be oxidized. In one embodiment, the heteroaromatic ring is selected from 5-8 membered monocyclic heteroaryl rings. The point of attachment of a heteroaromatic or heteroaryl ring to another group may be at either a carbon atom or a heteroatom of the heteroaromatic or heteroaryl rings.

As used herein, the term "heterocycle" refers collectively to heterocycloalkyl groups and heteroaryl groups.

As used herein, the term "heterocycloalkyl" refers to a monocyclic or polycyclic group having at least one heteroatom selected from O, N or S, and which has 2-11 carbon atoms, which may be saturated or unsaturated, but is not aromatic. Examples of heterocycloalkyl groups include, without being limited to, piperidinyl, piperazinyl, 2-oxopiperazinyl, 2-oxopiperidinyl, 2-oxopyrrolidinyl, 4-piperidonyl, pyrrolidinyl, hydantoinyl, valerolactamyl, oxiranyl, oxetanyl, tetrahydropyranyl, tetrahydrothiopyranyl, tetrahydropyrindinyl, tetrahydropyrimidinyl, tetrahydrothiopyranyl sulfone, tetrahydrothiopyranyl sulfoxide, morpholinyl, thiomorpholinyl, thiomorpholinyl sulfoxide, thiomorpholinyl sulfone, 1,3-dioxolane, tetrahydrofuranyl, dihydrofuranyl-2-one, tetrahydrothienyl, and tetrahydro-1, 1-dioxothienyl. Typically, monocyclic heterocycloalkyl groups have 3 to 7 members. Preferred 3 to 7 membered monocyclic heterocycloalkyl groups are those having 5 or 6 ring atoms. A heteroatom may be substituted with a protecting group known to those of ordinary skill in the art, for example, the hydrogen on a nitrogen may be substituted with a tert-butoxycarbonyl group. Furthermore, heterocycloalkyl groups may be optionally substituted with one or more substituents. In addition, the point of attachment of a heterocyclic ring to another group may be at either a carbon atom or a heteroatom of a heterocyclic ring. Only stable isomers of such substituted heterocyclic groups are contemplated in this definition.

As used herein, the term "substituent" or "substituted" means that a hydrogen radical on a compound or group is replaced with any desired group that is substantially stable to reaction conditions in an unprotected form or when protected using a protecting group. Examples of preferred substituents include, without being limited to, halogen (chloro, iodo, bromo, or fluoro); alkyl; alkenyl; alkynyl; hydroxy; alkoxy; nitro; thiol; thioether; imine; cyano; amido; phosphonato; phosphine; carboxyl; thiocarbonyl; sulfonyl; sulfonamide; ketone; aldehyde; ester; oxygen (—O); haloalkyl (e.g., trifluoromethyl); cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl), monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); $CO_2CH_3$; $CONH_2$; $OCH_2CONH_2$; $NH_2$; $SO_2NH_2$; $OCHF_2$; $CF_3$; $OCF_3$; and such moieties may also be optionally substituted by a fused-ring structure or bridge, for example $—OCH_2O—$. These substituents may optionally be further substituted with a substituent selected from such groups. In certain embodiments, the term "substituent" or the adjective "substituted" refers to a substituent selected from the group consisting of an alkyl, an alkenyl, an alkynyl, an cycloalkyl, an cycloalkenyl, a heterocycloalkyl, an aryl, a heteroaryl, an arylalkyl, a heteroarylalkyl, a haloalkyl, $—C(O)NR_{11}R_{12}$, $—NR_{13}C(O)R_{14}$, a halo, $—OR_{13}$, cyano, nitro, a haloalkoxy, $—C(O)R_{13}$, $—NR_{11}R_{12}$, $—SR_{13}$, $—C(O)OR_{13}$, $—OC(O)R_{13}$, $—NR_{13}C(O)NR_{11}R_{12}$, $—OC(O)NR_{11}R_{12}$, $—NR_{13}C(O)OR_{14}$, $—S(O)_rR_{13}$, $—NR_{13}S(O)_rR_{14}$, $—OS(O)_rR_{14}$, $S(O)_rNR_{11}R_{12}$, —O, —S, and $—N—R_{13}$, wherein r is 1 or 2; $R_{11}$ and $R_{12}$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted arylalkyl, or an optionally substituted heteroarylalkyl; or $R_{11}$ and $R_{12}$ taken together with the nitrogen to which they are attached is optionally substituted heterocycloalkyl or optionally substituted heteroaryl; and $R_{13}$ and $R_{14}$ for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted arylalkyl, or an optionally substituted heteroarylalkyl. In certain embodiments, the term "substituent" or the adjective "substituted" refers to a solubilizing group.

As used herein, the term "solubilizing group" refers to any group which can be substantially ionized and that enables the compound to be soluble in a desired solvent, such as, for example, water or water-containing solvent ("water-solubilizing group"). Furthermore, the solubilizing group can be one that increases the compound or complex's lipophilicity. In one embodiment, the solubilizing group is selected from alkyl group substituted with one or more heteroatoms such as N, O, S, each optionally substituted with alkyl group substituted independently with alkoxy, amino, alkylamino, dialkylamino, carboxyl, cyano, or substituted with cycloheteroalkyl or heteroaryl, or a phosphate, or a sulfate, or a carboxylic acid. In one embodiment, the solubilizing group is one of the following:

- an alkyl, cycloalkyl, aryl, heteroaryl group comprising either at least one nitrogen or oxygen heteroatom and/or which group is substituted by at least one amino group or oxo group (including, without being limited to, 2-oxopiperazinyl, 2-oxopiperidinyl, 2-oxopyrrolidinyl, 4-piperidonyl, hydantoinyl, valerolactamyl, oxiranyl, oxetanyl, tetrahydropyranyl, morpholinyl, 1,3-dioxolane, tetrahydrofuranyl and dihydrofuranyl-2-one);
- an amino group which may be a saturated cyclic amino group (including, without being limited to, piperidinyl, piperazinyl and pyrrolidinyl) which may be substituted by a group consisting of alkyl, alkoxycarbonyl, halogen, haloalkyl, hydroxyalkyl, amino, monoalkylamino, dialkylamino, carbamoyl, monoalkylcarbamoyl and dialkylcarbamoyl (including, without being limited to, methyl-piperidinyl, methyl-piperazinyl and methyl-pyrrolidinyl);
- one of the structures a) to i) shown below, wherein the wavy line and the arrow line correspond to the point of attachment to the core structure of the 2-aminoarylthiazole derivative of the invention, for example of formula (I) or (II):

a

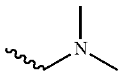

b

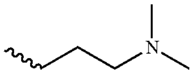

c

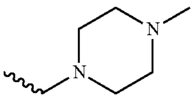

d

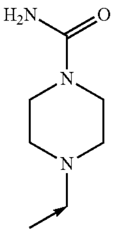

e

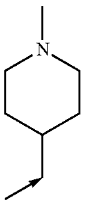

-continued f

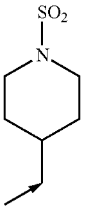

g

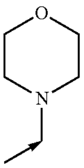

h

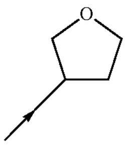

i

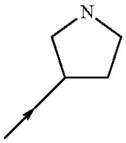

In one embodiment, the solubilizing group is one of the following:

- an alkyl, cycloalkyl, aryl, heteroaryl group comprising either at least one nitrogen or oxygen heteroatom or which group is substituted by at least one amino group or oxo group;
- an amino group which may be a saturated cyclic amino group which may be substituted by a group consisting of alkyl, alkoxycarbonyl, halogen, haloalkyl, hydroxyalkyl, amino, monoalkylamino, dialkylamino, carbamoyl, monoalkylcarbamoyl and dialkylcarbamoyl;
- one of the structures a) to i) shown above, wherein the wavy line and the arrow line correspond to the point of attachment to the core structure of the 2-aminoarylthiazole derivative of the invention, for example of formula (I) or (II).

In one embodiment, the solubilizing group is a saturated cyclic amino group (including, without being limited to, piperidinyl, piperazinyl and pyrrolidinyl) which may be substituted by a group consisting of alkyl, alkoxycarbonyl, halogen, haloalkyl, hydroxyalkyl, amino, monoalkylamino, dialkylamino, carbamoyl, monoalkylcarbamoyl and dialkylcarbamoyl (including, without being limited to, methyl-piperidinyl, methyl-piperazinyl and methyl-pyrrolidinyl).

In one embodiment, the solubilizing group is structure c) shown above, wherein the wavy line corresponds to the point of attachment to the core structure of the 2-aminoarylthiazole derivative of the invention, for example of formula (I) or (II).

As used herein, "pharmaceutically acceptable salt" refers to a salt of a free acid or a free base which is not biologically undesirable and is generally prepared by reacting the free base with a suitable organic or inorganic acid or by reacting the free acid with a suitable organic or inorganic base. Suitable acid addition salts are formed from acids that form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, napsylate, nicotinate, nitrate, orotate, oxalate, palmitate, pamoate, phosphate/hydrogen, phosphate/dihydrogen, phosphate, pyroglutamate, saccharate, stearate, succinate, tannate, tartrate, tosylate, trifluoroacetate and xinofoate salts. Suitable base salts are formed from bases that form non-toxic salts. Examples include the aluminum, arginine, benzathine, calcium, choline, diethylamine, diolamine, glycine, lysine, magnesium, meglumine, olamine, potassium, sodium, tromethamine, 2-(diethylamino) ethanol, ethanolamine, morpholine, 4-(2-hydroxyethyl) morpholine and zinc salts. Hemi salts of acids and bases may also be formed, e.g., hemi sulphate and hemi calcium salts.

In one embodiment, pharmaceutically acceptable salts are pharmaceutically acceptable acid addition salts, for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxy-ethane-sulfonic, in particular methanesulfonic acid, or aromatic sulfonic acids, for example benzene-, p-toluene- or naphthalene-2-sulfonic acid.

In one particular embodiment, the 2-aminoarylthiazole derivative of the invention or a pharmaceutically acceptable salt or solvate thereof is masitinib or a pharmaceutically acceptable salt or solvate thereof.

The chemical name for masitinib is 4-(4-methylpiperazin-1-ylmethyl)-N-[4-methyl-3-(4-pyridin-3ylthiazol-2-ylamino)phenyl]benzamide-CAS number 790299-79-5:

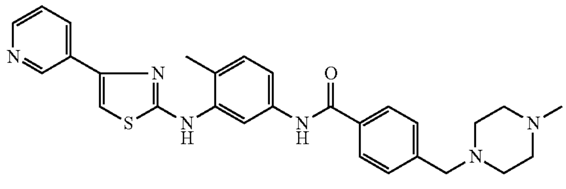 [SMILES: Cc1ccc(NC(=O)c2ccc(CN3CCN(C)CC3)cc2)cc1Nc1nc(-c2cccnc2)cs1]

Masitinib was first described in U.S. Pat. No. 7,423,055 and EP 1 525 200 B1.

In one embodiment, the 2-aminoarylthiazole derivative of the invention or a pharmaceutically acceptable salt or solvate thereof is masitinib mesilate. Thus, in one embodiment, the pharmaceutically acceptable salt of masitinib as described above is masitinib mesilate. As mentioned above, in other words, the pharmaceutically acceptable salt of masitinib is the methanesulfonic acid salt of masitinib.

A detailed procedure for the synthesis of masitinib mesilate is given in WO 2008/098949.

In one embodiment, "masitinib mesilate" refers to the orally bioavailable mesilate salt of masitinib-CAS 1048007-93-7 (MsOH); C28H30N6OS·$CH_3SO_3H$; MW 594.76:

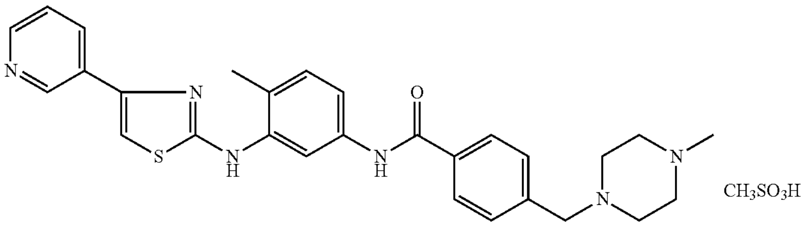

In one embodiment, the pharmaceutically acceptable salt of the 2-aminoarylthiazole derivative of the invention is mesilate.

Unless otherwise indicated, the term "mesilate" is used herein to refer to a salt of methanesulfonic acid with a named pharmaceutical substance (such as 2-aminoarylthiazole derivatives of formula (I) or (II)). Use of mesilate rather than mesylate is in compliance with the INNM (International nonproprietary names modified) issued by WHO (e.g., World Health Organization (February 2006). International Nonproprietary Names Modified. INN Working Document 05.167/3. WHO).

As used herein, "pharmaceutically acceptable solvate" refers to a molecular complex comprising the 2-aminoarylthiazole derivative of the invention and stoichiometric or sub-stoichiometric amounts of one or more pharmaceutically acceptable solvent molecules such as ethanol. The term 'hydrate' refers to when said solvent is water.

According to one embodiment, the 2-aminoarylthiazole derivative as described above, in particular masitinib, or a pharmaceutically acceptable salt or solvate thereof, is for administration at a therapeutically effective dose.

In one embodiment, the 2-aminoarylthiazole derivative as described above, in particular masitinib, or a pharmaceutically acceptable salt or solvate thereof, is for administration at a dose ranging from about 1 to about 12 mg/kg/day (mg per kilo body weight per day). In one embodiment, the 2-aminoarylthiazole derivative as described above, in particular masitinib, or a pharmaceutically acceptable salt or solvate thereof, is for administration at a dose ranging from about 1.5 to about 7.5 mg/kg/day. In one embodiment, the 2-aminoarylthiazole derivative as described above, in particular masitinib, or a pharmaceutically acceptable salt or solvate thereof, is for administration at a dose ranging from about 3 to about 12 mg/kg/day, preferably from about 3 to about 6 mg/kg/day.

In one embodiment, the 2-aminoarylthiazole derivative as described above, in particular masitinib, or a pharmaceutically acceptable salt or solvate thereof, is for administration at a dose of about 1, 2, 3, 4, 5, 6, 7, 8, 9, 10, 11, or 12 mg/kg/day. In one embodiment, the 2-aminoarylthiazole derivative as described above, in particular masitinib, or a pharmaceutically acceptable salt or solvate thereof, is for administration at a dose of about 1.5, 3, 4.5, 6, 7.5, 9, 10.5, or 12 mg/kg/day. In one embodiment, the 2-aminoarylthiazole derivative as described above, in particular masitinib, or a pharmaceutically acceptable salt or solvate thereof, is for administration at a dose of about 3, 4.5, or 6 mg/kg/day, preferably at a dose of about 6 mg/kg/day.

In one embodiment, the 2-aminoarylthiazole derivative as described above, in particular masitinib, or a pharmaceutically acceptable salt or solvate thereof, can be dose escalated by increments of about 1.5 mg/kg/day to reach a maximum of about 7.5 mg/kg/day, more preferably of about 4.5 or about 6 mg/kg/day. Each dose escalation is subjected to toxicity controls with an absence of any toxicity events permitting dose escalation to occur.

In one embodiment, the dose escalation of the 2-aminoarylthiazole derivative, in particular masitinib, or a pharmaceutically acceptable salt or solvate thereof, occurs at any time-point after at least 4 weeks after the administration of the initial dose and prior to 26 weeks after the administration of the initial dose; for example at 4 weeks, 8 weeks, 12 weeks, 16 weeks, 20 weeks, or 24 weeks after the administration of the initial dose, preferably at 12 weeks after the administration of the initial dose. Each dose escalation is subjected to toxicity controls, including for example: previous 4-week treatment period at a constant dose of study treatment and no suspected severe adverse event was reported and no suspected adverse event led to treatment interruption and no suspected adverse event is ongoing at the time of the dose increase, regardless of its severity.

In one embodiment, the 2-aminoarylthiazole derivative as described above, in particular masitinib, or a pharmaceutically acceptable salt or solvate thereof, is for administration at an initial dose of about 3 mg/kg/day during 6 weeks, then at a dose of about 4.5 mg/kg/day thereafter. In one embodiment, the 2-aminoarylthiazole derivative as described above, in particular masitinib, or a pharmaceutically acceptable salt or solvate thereof, is for administration at an initial dose of about 4.5 mg/kg/day during 6 weeks, then at a dose of about 6 mg/kg/day thereafter. In one embodiment, the 2-aminoarylthiazole derivative as described above, in particular masitinib, or a pharmaceutically acceptable salt or solvate thereof, is for administration at an initial dose of about 3 mg/kg/day during 12 weeks, then at a dose of about 4.5 mg/kg/day thereafter. In one embodiment, the 2-aminoarylthiazole derivative as described above, in particular masitinib, or a pharmaceutically acceptable salt or solvate thereof, is for administration at an initial dose of about 4.5 mg/kg/day during 12 weeks, then at a dose of about 6 mg/kg/day thereafter. In one embodiment, the 2-aminoarylthiazole derivative as described above, in particular masitinib, or a pharmaceutically acceptable salt or solvate thereof, is for administration at an initial dose of about 3 mg/kg/day during at least 4 weeks, then at a dose of about 4.5 mg/kg/day during at least 4 weeks, and at a dose of about 6 mg/kg/day thereafter, with each dose escalation being subjected to toxicity controls.

According to one embodiment, any dose indicated herein refers to the amount of active ingredient as such, not to its pharmaceutically acceptable salt or solvate form. Thus, compositional variations of a pharmaceutically acceptable salt or solvate of the 2-aminoarylthiazole derivative of the invention, in particular masitinib, will not impact the dose to be administered.

According to one embodiment, the 2-aminoarylthiazole derivative of the invention, in particular masitinib, or a pharmaceutically acceptable salt or solvate as described above, is adapted for an administration at a dose as described above.

According to one embodiment, the 2-aminoarylthiazole derivative as described above, preferably masitinib, or a pharmaceutically acceptable salt or solvate thereof, may be administered orally, intravenously, parenterally, topically, by inhalation in particular by inhalation spray, rectally, nasally, or buccally. In one embodiment, the 2-aminoarylthiazole derivative as described above, preferably masitinib, or a pharmaceutically acceptable salt or solvate thereof, is for oral administration.

In one embodiment, the 2-aminoarylthiazole derivative as described above, preferably masitinib, or a pharmaceutically acceptable salt or solvate thereof, is for administration at least once a day, preferably twice a day. In one embodiment, the 2-aminoarylthiazole derivative as described above, preferably masitinib, or a pharmaceutically acceptable salt or solvate thereof, is for prolonged administration, such as for example, for at least 1, 2, 3, 6, 9, or 12 months.

In one embodiment, the 2-aminoarylthiazole derivative as described above, preferably masitinib, or a pharmaceutically acceptable salt or solvate thereof, is adapted or is in a form adapted for oral administration. Examples of forms adapted for oral administration include, without being limited to, liquid, paste or solid compositions, and more particularly tablets, pills, capsules, liquids, gels, syrups, slurries, and suspensions.

In one embodiment, the 2-aminoarylthiazole derivative as described above, preferably masitinib, or a pharmaceutically acceptable salt or solvate thereof, is for administration as tablets, preferably as 100 mg or 200 mg tablets.

According to one embodiment, the 2-aminoarylthiazole derivative as described above, in particular masitinib, or a pharmaceutically acceptable salt or solvate thereof, is for administration with at least one further pharmaceutically active agent.

According to the present invention, the 2-aminoarylthiazole derivative as described above, in particular masitinib, or a pharmaceutically acceptable salt or solvate thereof, may be administered simultaneously, separately or sequentially with said at least one further pharmaceutically active agent.

In one embodiment, the 2-aminoarylthiazole derivative as described above, in particular masitinib, or a pharmaceutically acceptable salt or solvate thereof, is to be administered in combination with said at least one further pharmaceutically active agent, such as in a combined preparation, pharmaceutical composition or medicament.

In one embodiment, the 2-aminoarylthiazole derivative as described above, in particular masitinib, or a pharmaceutically acceptable salt or solvate thereof, and the at least one further pharmaceutically active agent are to be administered separately.

In one embodiment, said at least one further pharmaceutically active agent is selected from chemotherapeutic agents and corticoids.

In one embodiment, the 2-aminoarylthiazole derivative as described above, in particular masitinib, or a pharmaceutically acceptable salt or solvate thereof, is for administration with a chemotherapeutic agent. In one embodiment, said chemotherapeutic agent is docetaxel or cabazitaxel.

In one embodiment, the 2-aminoarylthiazole derivative as described above, in particular masitinib, or a pharmaceutically acceptable salt or solvate thereof, is for administration with docetaxel.

In one embodiment, the 2-aminoarylthiazole derivative as described above, in particular masitinib, or a pharmaceutically acceptable salt or solvate thereof, is for administration with at least one corticosteroid. Examples of corticosteroids include, but are not limited to, prednisone. In one embodiment, the 2-aminoarylthiazole derivative as described above, in particular masitinib, or a pharmaceutically acceptable salt or solvate thereof, is for administration with prednisone.

In one embodiment, the 2-aminoarylthiazole derivative as described above, in particular masitinib, or a pharmaceutically acceptable salt or solvate thereof, is for administration with a chemotherapeutic agent, such as docetaxel, and at least one corticosteroid, such as, for example, prednisone. In one embodiment, the 2-aminoarylthiazole derivative as described above, in particular masitinib, or a pharmaceutically acceptable salt or solvate thereof, is for administration with docetaxel and prednisone.

Another object of the present invention is a method for treating prostate cancer (preferably CRPC, more preferably mCRPC, and in particular early mCRPC associated with alkaline phosphatase (ALP) levels at baseline equal to or lower than 250 IU/L, and/or with a Halabi prognosis score (H) at baseline equal to or lower than 45) in a subject in need thereof as defined above, comprising administering to the subject a 2-aminoarylthiazole derivative, in particular masitinib, or a pharmaceutically acceptable salt or solvate thereof as described above.

In one embodiment, the method is for treating early mCRPC as defined herein.

In one embodiment, the method comprises administering a therapeutically effective dose of 2-aminoarylthiazole derivative as described above, in particular masitinib, or a pharmaceutically acceptable salt or solvate thereof.

In one embodiment, the method comprises administering at least one further pharmaceutically active agent as described herein. In one embodiment, said at least one further pharmaceutically active agent is selected from chemotherapeutic agents and corticoids.

Another object of the present invention is a pharmaceutical composition for treating or for use in the treatment of prostate cancer (preferably CRPC, more preferably mCRPC, and in particular early mCRPC associated with alkaline phosphatase (ALP) levels at baseline equal to or lower than 250 IU/L, and/or with a Halabi prognosis score (H) at baseline equal to or lower than 45) in a subject in need thereof as defined above, said pharmaceutical composition comprising a 2-aminoarylthiazole derivative, in particular masitinib, or a pharmaceutically acceptable salt or solvate thereof as described above and optionally at least one pharmaceutically acceptable excipient.

In one embodiment, the pharmaceutical composition is for treating or for use in the treatment of early mCRPC as defined herein.

In one embodiment, the pharmaceutical composition is for administration with at least one further pharmaceutically active agent as described herein. According to the present invention, the pharmaceutical composition may be administered simultaneously, separately or sequentially with said at least one further pharmaceutically active agent. In one embodiment, said at least one further pharmaceutically active agent is selected from chemotherapeutic agents and corticoids.

Another object of the present invention is the use of a 2-aminoarylthiazole derivative, in particular masitinib, or a pharmaceutically acceptable salt or solvate thereof as described above, for the manufacture of a medicament for the treatment of prostate cancer (preferably CRPC, more preferably mCRPC, and in particular early mCRPC associated with alkaline phosphatase levels at baseline equal to or lower than 250 IU/L, and/or with a Halabi prognosis score (H) at baseline equal to or lower than 45) in a subject in need thereof as defined above.

In one embodiment, the present invention relates to the use of a 2-aminoarylthiazole derivative, in particular masitinib, or a pharmaceutically acceptable salt thereof as described above, for the manufacture of a medicament for the treatment of early mCRPC as defined herein.

In one embodiment, the medicament is for administration with at least one further pharmaceutically active agent as described herein. According to the present invention, the medicament may be administered simultaneously, separately or sequentially with said at least one further pharmaceutically active agent. In one embodiment, said at least one further pharmaceutically active agent is selected from chemotherapeutic agents and corticoids.

EXAMPLES

The present invention is further illustrated by the following examples.

Example 1

Materials and Methods

A prospective, multicenter, randomized, double blind, placebo-controlled, 2-parallel groups, phase 3 study was conducted to assess the efficacy and safety of masitinib in combination with docetaxel as compared to placebo in combination with docetaxel in first line metastatic castrate-resistant prostate cancer (mCRPC).

The objective of the study was to assess the efficacy and safety of masitinib in combination with docetaxel as compared to docetaxel in combination with placebo in first line metastatic castrate-resistant prostate cancer (mCRPC). Efficacy was assessed based on the progression-free survival (PFS), measured in months.

The patients recruited in the study consist of adult males suffering from prostate cancer who progressed to develop castration-resistant prostate cancer (CRPC) after castration treatment (reduction of androgens (e.g., testosterone, dihydrotestosterone (DHT)) by chemical or surgical means). These patients are considered to be patients in the first line metastatic castration-resistant prostate cancer (mCRPC).

The patients recruited in the study were randomized in two groups with a ratio 1:1:

Group 1: masitinib (6 mg/kg/day)+docetaxel (75 mg/$m^2$ 6 cycles—8 or 10 cycles possible)+prednisone according to usual practice;

Group 2: placebo+docetaxel (75 mg/$m^2$ 6 cycles—8 or 10 cycles possible)+prednisone according to usual practice.

Docetaxel was combined with prednisone as usual practice.

Patients were centrally randomized to one of the two treatment groups by IWRS (Interactive Web Response System) according to minimization method.

Inclusion criteria were:

Patient aged≥18 years old, with histologically or cytologically confirmed metastatic castrate-resistant prostate cancer (medical or surgical castration: androgens deprivation by GnRH agonist or antagonist or patient with surgical castration; hormonal castration confirmed biologically (testosterone<0.5 ng/ml) with one of the following criteria:

If surgical castration is done than there is no requirement to perform testosterone test.

Pre-treated with abiraterone with progressed disease documented, OR

With indication for initiating docetaxel administration (e.g., widespread visceral disease or rapidly progressive disease).

Patient with evidence of progressive metastatic disease. Disease progression at trial enrolment is based on progression in at least one variable as described in the Prostate Cancer Clinical Trials Working Group (PCWG2) definition of response and progression for disease manifestations in prostate cancer (Scher et al. J Clin Oncol. 2008; 26:1148-1159):

| Variable | Definition of Response and Progression |
| --- | --- |
| PSA (prostate-specific antigen) | Favorable effect on PSA may be delayed for 12 weeks or more. An effort is made not to discontinue therapy solely on the basis of a rise in PSA in the absence of other indicators of disease progression.<br>Ignore early rises (prior to 12 weeks) in determining PSA response.<br>Record the percent change from baseline (rise or fall) at 12 weeks, and separately, the maximal change (rise or fall) at any time using a waterfall plot.<br>Response<br>Decline of ≥50% from baseline confirmed by a second value at least 3 weeks later.<br>Time to PSA progression is defined according to PCWG2<br>For patients whose PSA has initially decreased, progression is defined as the first PSA increase that is ≥25% above the nadir and >2 ng/ml above the nadir and which is confirmed after 3 or moreweeks later sequentially.<br>For patients whose PSA has not decreased, progression is defined as the first PSA increase that is >25% above the nadir and ≥2 ng/ml above the baseline and which is confirmed after 3 or more weeks later sequentially.<br>As per PCWG2, increase in PSA within the first 12 weeks of treatment will not be considered as progression. |
| Soft-tissue lesion (nodal and visceral) | Use-RECIST (Response Evaluation Criteria in Solid Tumors) 1.1(Eisenhauer *et al.* European Journal of Cancers 45: 228-247, 2009) with caveats<br>Only report changes in lymph nodes that were ≥2 cm in diameter at baseline.<br>Record changes in nodal and visceral soft tissue sites separately.<br>Record complete elimination of disease at any site separately.<br>Confirm responses with second scan 6-8 weeks later; for progression, no confirmation is needed.<br>Response<br>Use RECIST 1.1 for response evaluation of nodal and visceral lesions.<br>Progression<br>Use RECIST 1.1 criteria for progression. |
| Bone | Use -RECIST 1.1 and PCWG2<br>Response<br>Use RECIST 1.1 and PCWG2<br>Progression<br>The occurrence of 2 new bone lesions. Use RECIST 1.1 and PCWG2.<br>Confirmation is needed at week 12. |
| Symptoms (pain and analgesic consumption) | Consider independently of other outcome measures.<br>Document pain and analgesia at baseline and measure repeatedly at 4-week intervals.<br>Ignore early changes (≤12 weeks) in pain in absence of compelling evidence of disease progression.<br>Confirm response or progression of pain end points 3 weeks later.<br>Response<br>Reduction in the present pain intensity (PPI) score by two points without an increase in the analgesic score, or reduction of at least 50% in the analgesic score without an increase in the PPI score.<br>Response has to be maintained for at least three weeks.<br>Progression<br>Increase PPI score of at least one point from nadir and an increase from baseline of at least 25% in analgesic score, or a requirement for palliative radiotherapy and confirmed three weeks later.<br>Increase in PPI score within the first 12 weeks of treatment will not be considered as progression. |

Patient with ECOG≤1

Patient with adequate organ function:

Absolute neutrophil count (ANC)≥$1.5\times10^9$/L

Hemoglobin≥10 g/dL

Platelets (PTL)≥$75\times10^9$/L

AST (aspartate aminotransferase)/ALT (alanine aminotransferase)≤3× upper limit of normal or ULN (≤5× ULN in case of liver metastases)

Gamma glutamyl transferase (GGT)≤2.5×ULN (≤5×ULN in case of liver metastases)

Bilirubin≤1.5×ULN (≤3×ULN in case of liver metastasis)

Normal creatinine or if abnormal creatinine, creatinine clearance≥50 mL/min (Cockcroft and Gault formula)

Urea≤2×ULN

Albumin>1×LLN (lower limit of normal)

Proteinuria<30 mg/dL (1+) on the dipstick; in case of proteinuria≥1+on the dipstick, 24 hours proteinuria must be ≤1.5 g/24 h Patient with life expectancy>3 months Patient with BMI>18 kg/$m^2$ and patient weight>40 kg Male patient with a female partner of childbearing potential who agrees to use a highly effective method of contraception and an acceptable method of contraception by his female partner during the study and for 3 months after the last treatment intake or who agrees to use an acceptable method of contraception and a highly effective method of contraception by his female partner during the study and for 3 months after the last treatment intake.

Exclusion criteria were:

Patient who has been previously treated with chemotherapy.

Patient with bone marrow irradiation>40% within 12 months before baseline

Patient treated for a cancer other than prostate cancer within 3 years before enrolment, with the exception of basal cell carcinoma (and pTa or pT1 tumors)

Patient with active central nervous system (CNS) metastasis or with history of CNS metastasis Patient presenting with cardiac disorders defined by at least one of the following conditions:

Patient with recent cardiac history (within 6 months) of:

Acute coronary syndrome

Acute heart failure (class III or IV of the New York Heart Association (NYHA) classification)

Significant ventricular arrhythmia (persistent ventricular tachycardia, ventricular fibrillation, resuscitated sudden death)

Patient with cardiac failure class III or IV of the NYHA classification

Patient with severe conduction disorders which are not prevented by permanent pacing (atrio-ventricular block 2 and 3, sino-atrial block)

Syncope without known etiology within 3 months

Uncontrolled severe hypertension, according to the judgement of the investigator, or symptomatic hypertension Patient with an history of poor compliance or an history of drug/alcohol abuse, or excessive alcohol beverage consumption that would interfere with the ability to comply with the study protocol, or current or past psychiatric disease that might interfere with the ability to comply with the study protocol or give informed consent Patient under treatment with any anti-tumor therapy (any radiotherapy, chemotherapy, biologic or anti-androgen therapy except GnRH/LHRH analogs).

For each patient included in the study, the Halabi prognosis score also referred to as (H) (i.e., survival estimate) was calculated using the following formula:

$$H=[0.392\times(2 \text{ if ECOG}=2,\ 1 \text{ if ECOG}=1,\ 0 \text{ if ECOG}=0)]+[0.335\times(1 \text{ if Gleason Score in } [8\text{-}10],\ 0 \text{ if Gleason Score}<8)]+[\exp(0.312\times\log(LDH)+0.211\times\log(AP)+0.093\times\log(PSA))]+[0.161\times(1 \text{ if presence of Visceral Disease, else } 0)]-[0.082\times HB].$$

As used herein, the Halabi prognosis score (H) is based on the method described by Halabi et al. (J Clin Oncol. 2003 Apr. 1; 21 (7): 1232-7) and is used as an estimate of patient survival. As described above, the mathematic formula is based on the measurement of visceral disease (yes or no, the value of this parameter being equal to 1 if the subject is affected with visceral disease, and 0 if he is not), initial Gleason score (the value being equal to 1 if the Gleason score measured for the subject ranges from 8 to 10, and 0 if the Gleason score is inferior to 8), ECOG (Eastern Cooperative Oncology Group) performance status (ranging from 0 to 2), prostate specific antigen (PSA) levels (PSA, measured in ng/mL), lactic acid dehydrogenase (LDH) levels (LDH, measured in IU/L), alkaline phosphatase (ALP) levels (ALP or AP, measured in IU/L) and hemoglobin (HB, measured in g/dL).

In particular, the Halabi prognosis score (H) was calculated using the following procedure for a subject having an ECOG performance status of 0 or 1:

VISCERAL1: enter if the patient has been diagnosed with visceral disease (Yes/No) (VISCERAL_n).

ECOG1: enter the patient's ECOG value (0 versus 1 versus 2) (ecog_SCR).

GLEASON11: enter the patient's Gleason value-should be a whole number from the range: [2-10] (QSSCORE).

LDH1: enter the patient's LDH value-should be a decimal number from the range: [6-4000 IU/L] (ldh_SCR).

AP1: enter the patient's Alkaline Phosphatase value (AP1)—should be a decimal number from the range: [10-2500 IU/L] (SCREEN_LOCALV)

HB1: enter the patient's Hemoglobin value-should be a decimal number from the range: [10-20 g/dl] (HEMO_SCR).

PSA1: enter the patient's PSA value-should be a decimal number from the range: [0.0001-5000 ng/ml] (PSA_SCR).

Based on these values, the Interactive Web Response System used for randomization calculated the Halabi prognosis score (H) using the following Statistical Analysis System (SAS) program code:

```
HALABI Score Derive;
if QSSCORE<8 then GLEASON1=0;
else if 8<=QSSCORE<=10 then GLEASON1=1;
else GLEASON1=.;
ECOG1=0.392*ecog_SCR;
GLEASON11=0.335*GLEASON1;
LDH1=0.312*(log (ldh_SCR));
AP1=0.211*(log (SCREEN_LOCALV));
PSA1=0.093*(log (PSA_SCR));
VISCERAL1=0.161*VISCERAL_n;
HB1=0.082*HEMO_SCR;
d1=exp (LDH1+AP1+PSA1);
H=(ECOG1+GLEASON11+d1+VISCERAL1-HB1).
```

Below is a worked example using patient data (001-003) with the following values:

ECOG1=0 (i.e., ECOG 0)

GLEASON11=1 (i.e., Gleason score 8-10)

LDH1=184

AP1=88

PSA1=3.9

VISCERAL1=1 (i.e., visceral disease)

HB1=13.0

Hence, for this patient:

$$H=[0.392*0]+[0.335*1]+[\exp(0.312*(\log(184))+0.211*(\log(88))+0.093*(\log(3.90)))]+[0.161*1]-[0.082*13.0]=14.29$$

Results

The efficacy of masitinib for treating mCRPC was assessed based on the progression-free survival (expressed by the median progression-free survival measured in months ("Median"), accompanied by the related 95% confidence interval ("95% CI") and p-value), and on two parameters measured in the subject population. First, a hazard ratio (HR) is measured, corresponding to the probability of death when treated with masitinib (+docetaxel+prednisone) over the probability of death when treated with placebo (+docetaxel+prednisone). Thus, a HR<1 indicates that the probability of death when treated with masitinib is lower than the probability of death when treated with placebo (and is thus indicative of a therapeutic benefit). Second, a "Risk benefit" is measured, allowing to assess the effect of masitinib in a specific subgroup, as compared to the mirror subgroup.

The results obtained first demonstrate that the therapeutic benefit of masitinib is dependent on the alkaline phosphatase (ALP) levels measured at baseline in the subject, as shown in Tables 1-4 below.

TABLE 1

Masitinib treatment effect in terms of median PFS (in months) according to baseline ALP levels equal to or lower than 250 IU/L

| Targeted group | Treatment group | Number of Subjects | Median [95% CI] | P-value Log Rank | Hazard Ratio (95% CI) | Risk Benefit |
|---|---|---|---|---|---|---|
| ALP ≤ 250 | MASITINIB | 225 | 6.3 [5.6; 7.6] | 0.0272 | 0.79 [0.65; 0.96] | 21% |
| ALP ≤ 250 | PLACEBO | 225 | 5.4 [4.8; 6.0] | | | |
| ALP > 250 | MASITINIB | 130 | 4.2 [3.5; 5.5] | 0.1306 | 1.20 [0.93; 1.55] | |
| ALP > 250 | PLACEBO | 132 | 5.5 [4.3; 6.1] | | | |

TABLE 2

Masitinib treatment effect in terms of median PFS (in months) according to baseline ALP levels equal to or lower than 200 IU/L

| Targeted group | Treatment group | Number of Subjects | Median [95% CI] | P-value Log Rank | Hazard Ratio (95% CI) | Risk Benefit |
|---|---|---|---|---|---|---|
| ALP ≤ 200 | MASITINIB | 178 | 6.9 [5.8; 7.9] | 0.0126 | 0.73 [0.58; 0.91] | 27% |
| ALP ≤ 200 | PLACEBO | 176 | 5.6 [4.6; 6.2] | | | |
| ALP > 200 | MASITINIB | 177 | 4.4 [4.1; 5.5] | 0.1753 | 1.17 [0.94; 1.45] | |
| ALP > 200 | PLACEBO | 181 | 5.1 [4.4; 5.8] | | | |

TABLE 3

Masitinib treatment effect in terms of median PFS (in months) according to baseline ALP levels equal to or lower than 150 IU/L

| Targeted group | Treatment group | Number of Subjects | Median [95% CI] | P-value Log Rank | Hazard Ratio (95% CI) | Risk Benefit |
|---|---|---|---|---|---|---|
| ALP ≤ 150 | MASITINIB | 134 | 6.9 [5.6; 8.5] | 0.0008 | 0.63 [0.48; 0.82] | 37% |
| ALP ≤ 150 | PLACEBO | 133 | 5.5 [4.6; 6.9] | | | |
| ALP > 150 | MASITINIB | 221 | 4.9 [4.2; 5.8] | 0.229 | 1.14 [0.94; 1.39] | |
| ALP > 150 | PLACEBO | 224 | 5.1 [4.4; 5.8] | | | |

TABLE 4

Masitinib treatment effect in terms of median PFS (in months) according to baseline ALP levels equal to or lower than 100 IU/L

| Targeted group | Treatment group | Number of Subjects | Median [95% CI] | P-value Log Rank | Hazard Ratio (95% CI) | Risk Benefit |
|---|---|---|---|---|---|---|
| ALP ≤ 100 | MASITINIB | 59 | 9.0 [7.6; 10.7] | 0.0022 | 0.53 [0.35; 0.79] | 47% |
| ALP ≤ 100 | PLACEBO | 72 | 6.9 [5.5; 7.9] | | | |

TABLE 4-continued

| Masitinib treatment effect in terms of median PFS (in months) according to baseline ALP levels equal to or lower than 100 IU/L | | | | | | |
|---|---|---|---|---|---|---|
| Targeted group | Treatment group | Number of Subjects | Median [95% CI] | P-value Log Rank | Hazard Ratio (95% CI) | Risk Benefit |
| ALP > 100 | MASITINIB | 296 | 5.4 [4.3; 5.9] | 0.9943 | 1.02 [0.86; 1.22] | |
| ALP > 100 | PLACEBO | 285 | 4.9 [4.2; 5.6] | | | |

As shown in Table 1, patients with ALP levels at baseline equal to or lower than 250 IU/L show an increased response to masitinib. In addition, as shown in Tables 1-4, lower ALP levels at baseline are associated with an improved hazard ratio (reaching 0.53 for ALP levels at baseline equal to or lower than 100 IU/L) corresponding to an increased risk benefit (reaching 47% for ALP levels at baseline equal to or lower than 100 IU/L).

Second, the results obtained demonstrate that the therapeutic benefit of masitinib is dependent on the Halabi score (H) measured at baseline in the subject, as shown in Table 5 below.

TABLE 5

| Masitinib treatment effect in terms of median PFS (in months) according to the Halabi prognosis score (H) at baseline | | | | | | |
|---|---|---|---|---|---|---|
| Targeted group | Treatment group | Number of Subjects | Median [95% CI] | P-value Log Rank | Hazard Ratio (95% CI) | Risk Benefit |
| H ≤ 15 | MASITINIB | 17 | 15 [6.2; 30.5] | 0.0051 | 0.28 [0.10; 0.81] | 72% |
| | PLACEBO | 18 | 5.9 [3.7; 9.7] | | | |
| H > 15 | MASITINIB | 338 | 5.5 [4.8; 6.2] | 0.7264 | 0.99 [0.84; 1.16] | 1% |
| | PLACEBO | 339 | 5.3 [4.8; 5.8] | | | |
| H ≤ 16 | MASITINIB | 29 | 9.0 [5.5; 21.2] | 0.0089 | 0.35 [0.16; 0.77] | 65% |
| | PLACEBO | 24 | 6.2 [4.9; 9.7] | | | |
| H > 16 | MASITINIB | 326 | 5.5 [4.8; 6.2] | 0.8063 | 1.00 [0.85; 1.17] | 0% |
| | PLACEBO | 333 | 5.1 [4.8; 5.8] | | | |
| H ≤ 17 | MASITINIB | 41 | 7.0 [5.5; 14.5] | 0.0229 | 0.49 [0.28; 0.87] | 51% |
| | PLACEBO | 35 | 7.3 [4.9; 9.7] | | | |
| H > 17 | MASITINIB | 314 | 5.5 [4.8; 6.2] | 0.8357 | 1.00 [0.85; 1.18] | 0% |
| | PLACEBO | 322 | 5.0 [4.6; 5.7] | | | |
| H ≤ 18 | MASITINIB | 50 | 7.0 [5.5; 11.8] | 0.0152 | 0.54 [0.33; 0.87] | 46% |
| | PLACEBO | 43 | 6.2 [4.9; 8.3] | | | |
| H > 18 | MASITINIB | 305 | 5.5 [4.8; 6.1] | 0.9071 | 1.00 [0.85; 1.19] | 0% |
| | PLACEBO | 314 | 5.0 [4.6; 5.7] | | | |
| H ≤ 19 | MASITINIB | 70 | 6.9 [5.6; 9.0] | 0.076 | 0.69 [0.48; 1.00] | 31% |
| | PLACEBO | 64 | 5.9 [4.2; 7.6] | | | |
| H > 19 | MASITINIB | 285 | 5.4 [4.2; 6.1] | 0.8777 | 1.00 [0.84; 1.19] | 0% |
| | PLACEBO | 293 | 5.1 [4.8; 5.8] | | | |
| H ≤ 20 | MASITINIB | 86 | 7.0 [5.8; 9.7] | 0.0145 | 0.65 [0.46; 0.90] | 36% |
| | PLACEBO | 84 | 6.2 [4.9; 7.6] | | | |

TABLE 5-continued

Masitinib treatment effect in terms of median PFS (in months) according to the Halabi prognosis score (H) at baseline

| Targeted group | Treatment group | Number of Subjects | Median [95% CI] | P-value Log Rank | Hazard Ratio (95% CI) | Risk Benefit |
|---|---|---|---|---|---|---|
| H > 20 | MASITINIB | 269 | 4.9 [4.2; 5.9] | 0.8172 | 1.04 [0.87; 1.24] | −4% |
| | PLACEBO | 273 | 4.9 [4.4; 5.6] | | | |
| H ≤ 21 | MASITINIB | 101 | 7.0 [5.6; 8.9] | 0.0066 | 0.65 [0.48; 0.88] | 35% |
| | PLACEBO | 97 | 5.8 [4.9; 7.0] | | | |
| H > 21 | MASITINIB | 254 | 4.9 [4.2; 5.8] | 0.6164 | 1.07 [0.89; 1.28] | −7% |
| | PLACEBO | 260 | 4.9 [4.4; 5.8] | | | |
| H ≤ 22 | MASITINIB | 116 | 6.9 [5.6; 8.5] | 0.0034 | 0.65 [0.49; 0.87] | 35% |
| | PLACEBO | 115 | 5.9 [4.9; 6.9] | | | |
| H > 22 | MASITINIB | 239 | 4.9 [4.2; 5.8] | 0.4837 | 1.09 [0.90; 1.32] | −9% |
| | PLACEBO | 242 | 4.9 [4.2; 5.6] | | | |
| H ≤ 27 | MASITINIB | 203 | 6.5 [5.5; 7.6] | 0.0099 | 0.75 [0.61; 0.93] | 25% |
| | PLACEBO | 203 | 5.6 [4.9; 6.2] | | | |
| H > 27 | MASITINIB | 152 | 4.8 [4.1; 5.8] | 0.1129 | 1.20 [0.95; 1.51] | −20% |
| | PLACEBO | 154 | 4.9 [4.2; 6.0] | | | |
| H ≤ 33 | MASITINIB | 265 | 6.4 [5.6; 7.6] | 0.0187 | 0.81 [0.67; 0.97] | 19% |
| | PLACEBO | 269 | 5.6 [4.9; 6.0] | | | |
| H > 33 | MASITINIB | 90 | 4.1 [3.4; 4.9] | 0.0297 | 1.34 [0.98; 1.82] | −34% |
| | PLACEBO | 88 | 5.0 [4.2; 6.0] | | | |

As shown in Table 5, patients with a Halabi prognosis score (H) at baseline equal to or lower than 33 show an increased response to masitinib. In addition, the therapeutic benefit of masitinib increases when the Halabi score (H) at baseline decreases.

Moreover, and as shown in Tables 6-10, the therapeutic benefit of masitinib is increased in patients presenting both low ALP levels measured at baseline (i.e., ALP levels at baseline equal to or lower than 250 IU/L), and a low Halabi score (H) measured at baseline (i.e., a Halabi prognosis score (H) at baseline equal to or lower than 33).

TABLE 6

Masitinib treatment effect in terms of median PFS (in months) according to baseline ALP levels equal to or lower than 250 IU/L and to a Halabi prognosis score (H) at baseline equal to or lower than 18

| Targeted group | Treatment group | Number of Subjects | Median [95% CI] | P-value Log Rank | Hazard Ratio (95% CI) | Risk Benefit |
|---|---|---|---|---|---|---|
| ALP ≤ 250 and H ≤ 18 | MASITINIB | 49 | 7.7 [5.5; 11.8] | 0.0098 | 0.52 [0.32; 0.84] | 48% |
| | PLACEBO | 41 | 5.9 [4.2; 7.6] | | | |
| ALP ≤ 250 and H > 18 | MASITINIB | 176 | 6.2 [5.4; 7.6] | 0.2513 | 0.87 [0.69; 1.08] | |
| | PLACEBO | 184 | 4.9 [4.2; 6.0] | | | |

TABLE 6-continued

Masitinib treatment effect in terms of median PFS (in months) according to baseline ALP levels equal to or lower than 250 IU/L and to a Halabi prognosis score (H) at baseline equal to or lower than 18

| Targeted group | Treatment group | Number of Subjects | Median [95% CI] | P-value Log Rank | Hazard Ratio (95% CI) | Risk Benefit |
|---|---|---|---|---|---|---|
| ALP > 250 and H ≤ 18 | MASITINIB | 1 | 3.4 | 0.1573 | Not applicable | |
| | PLACEBO | 2 | 10 [9.9; 10.4] | | | |
| ALP > 250 and H > 18 | MASITINIB | 129 | 4.3 [3.5; 5.5] | 0.1647 | 1.19 [0.92; 1.53] | |
| | PLACEBO | 130 | 5.5 [4.2; 5.9] | | | |

TABLE 7

Masitinib treatment effect in terms of median PFS (in months) according to baseline ALP levels equal to or lower than 250 IU/L and to a Halabi prognosis score (H) at baseline equal to or lower than 19

| Targeted group | Treatment group | Number of Subjects | Median [95% CI] | P-value Log Rank | Hazard Ratio (95% CI) | Risk Benefit |
|---|---|---|---|---|---|---|
| ALP ≤ 250 and H ≤ 19 | MASITINIB | 66 | 6.9 [5.6; 8.9] | 0.0295 | 0.66 [0.45; 0.96] | 34% |
| | PLACEBO | 61 | 5.6 [4.2; 7.5] | | | |
| ALP ≤ 250 and H > 19 | MASITINIB | 159 | 6.1 [4.8; 7.6] | 0.2548 | 0.86 [0.68; 1.09] | |
| | PLACEBO | 164 | 4.9 [4.2; 6.0] | | | |
| ALP > 250 and H ≤ 19 | MASITINIB | 4 | 9.2 [2.3; 20.5] | 0.4752 | Not applicable | |
| | PLACEBO | 3 | 10 [9.9; 35.3] | | | |
| ALP > 250 and H > 19 | MASITINIB | 126 | 4.2 [3.5; 5.4] | 0.1841 | 1.18 [0.91; 1.52] | |
| | PLACEBO | 129 | 5.3 [4.2; 5.9] | | | |

TABLE 8

Masitinib treatment effect in terms of median PFS (in months) according to baseline ALP levels equal to or lower than 250 IU/L and to a Halabi prognosis score (H) at baseline equal to or lower than 20

| Targeted group | Treatment group | Number of Subjects | Median [95% CI] | P-value Log Rank | Hazard Ratio (95% CI) | Risk Benefit |
|---|---|---|---|---|---|---|
| ALP ≤ 250 and H ≤ 20 | MASITINIB | 81 | 7.0 [5.6; 9.0] | 0.0057 | 0.62 [0.44; 0.87] | 38% |
| | PLACEBO | 80 | 5.9 [4.9; 7.5] | | | |
| ALP ≤ 250 and H > 20 | MASITINIB | 144 | 5.8 [4.4; 7.6] | 0.4607 | 0.90 [0.70; 1.15] | |
| | PLACEBO | 145 | 4.9 [4.1; 6.0] | | | |
| ALP > 250 and H ≤ 20 | MASITINIB | 5 | 13 [2.3; 20.5] | 0.7166 | 1.78 [0.28; 11.49] | |
| | PLACEBO | 4 | 10 [7.0; 35.3] | | | |
| ALP > 250 and H > 20 | MASITINIB | 125 | 4.2 [3.5; 5.4] | 0.1598 | 1.19 [0.92; 1.54] | |
| | PLACEBO | 128 | 5.3 [4.2; 5.9] | | | |

TABLE 9

Masitinib treatment effect in terms of median PFS (in months) according to baseline ALP levels equal to or lower than 250 IU/L and to a Halabi prognosis score (H) at baseline equal to or lower than 21

| Targeted group | Treatment group | Number of Subjects | Median [95% CI] | P-value Log Rank | Hazard Ratio (95% CI) | Risk Benefit |
|---|---|---|---|---|---|---|
| ALP ≤ 250 and | MASITINIB | 95 | 7.0 [5.6; 8.9] | 0.0027 | 0.62 [0.45; 0.85] | 38% |
| H < 21 | PLACEBO | 91 | 5.7 [4.9; 7.0] | | | |
| ALP ≤ 250 and | MASITINIB | 130 | 5.8 [4.2; 7.2] | 0.6706 | 0.94 [0.72; 1.22] | |
| H > 21 | PLACEBO | 134 | 4.9 [3.9; 6.0] | | | |
| ALP > 250 and | MASITINIB | 6 | 8.3 [2.3; 20.5] | 0.7598 | 0.99 [0.25; 3.88] | |
| H ≤ 21 | PLACEBO | 6 | 8.4 [4.2; 35.3] | | | |
| ALP > 250 and | MASITINIB | 124 | 4.2 [3.5; 5.4] | 0.1613 | 1.19 [0.92; 1.54] | |
| H > 21 | PLACEBO | 126 | 5.3 [4.2; 5.9] | | | |

TABLE 10

Masitinib treatment effect in terms of median PFS (in months) according to baseline ALP levels equal to or lower than 250 IU/L and to a Halabi prognosis score (H) at baseline equal to or lower than 22

| Targeted group | Treatment group | Number of Subjects | Median [95% CI] | P-value Log Rank | Hazard Ratio (95% CI) | Risk Benefit |
|---|---|---|---|---|---|---|
| ALP ≤ 250 and | MASITINIB | 110 | 6.9 [5.6; 8.3] | 0.0016 | 0.63 [0.47; 0.85] | 37% |
| H < 22 | PLACEBO | 107 | 5.8 [4.9; 6.7] | | | |
| ALP ≤ 250 and | MASITINIB | 115 | 5.8 [4.2; 7.2] | 0.8419 | 0.97 [0.73; 1.28] | |
| H > 22 | PLACEBO | 118 | 4.8 [3.6; 6.0] | | | |
| ALP > 250 and | MASITINIB | 6 | 8.3 [2.3; 20.5] | 0.9411 | 0.88 [0.26; 2.96] | |
| H ≤ 22 | PLACEBO | 8 | 7.5 [3.5; 10.4] | | | |
| ALP > 250 and | MASITINIB | 124 | 4.2 [3.5; 5.4] | 0.1565 | 1.20 [0.92; 1.55] | |
| H > 22 | PLACEBO | 124 | 5.3 [4.2; 5.9] | | | |

Similar results were obtained in patients presenting ALP levels at baseline lower than 250 IU/L. For example, in the group of patients presenting ALP levels at baseline equal to or lower than 200 IU/L and a Halabi prognosis score (H) equal to or lower than 18 at baseline, the measured hazard ratio is of about 0.5 and the risk benefit of about 50%. In the group of patients with ALP levels at baseline equal to or lower than 150 IU/L and a Halabi prognosis score (H) equal to or lower than 18 at baseline, these values are respectively of 0.46 and 55%, and of 0.46 and 56% in the group of patients with ALP levels at baseline equal to or lower than 100 IU/L and a Halabi prognosis score (H) equal to or lower than 18 at baseline.

Altogether, these data demonstrate a strong benefit effect of masitinib for treating mCRPC in patients presenting low ALP levels at baseline (e.g., equal to or lower than 250 IU/L) and/or a low Halabi score (H) at baseline (e.g., equal to or lower than 33).

The invention claimed is:

1. A method for treating metastatic castrate-resistant prostate cancer (mCRPC) in a subject in need thereof, said method comprising administering to the subject masitinib, or a pharmaceutically acceptable salt or solvate thereof, wherein said subject suffers from early mCRPC associated (i) with alkaline phosphatase (ALP) levels at baseline equal to or lower than 250 IU/L, or (ii) with a Halabi prognosis score (H) at baseline equal to or lower than 33, or (iii) with ALP levels at baseline equal to or lower than 250 IU/L and with a Halabi prognosis score (H) at baseline equal to or lower than 33.

2. The method according to claim 1, wherein said subject has ALP levels at baseline equal to or lower than 240, 230, 220, 210, 200, 190, 180, 170, 160, 150, 140, 130, 120, 110, or 100 IU/L.

3. The method according to claim 1, wherein said subject has ALP levels at baseline equal to or lower than 200 IU/L.

4. The method according to claim 1, wherein said subject has ALP levels at baseline equal to or lower than 150 IU/L.

5. The method according to claim 1, wherein said subject has ALP levels at baseline equal to or lower than 100 IU/L.

6. The method according to claim 1, wherein said subject has a Halabi prognosis score (H) at baseline equal to or lower than 32, 31, 30, 29, 28, 27, 26, 25, 24, 23, 22, 21, 20, 19, 18, 17, 16, or 15.

7. The method according to claim 1, wherein said subject has a Halabi prognosis score (H) at baseline equal to or lower than 22.

8. The method according to claim 1, wherein said subject received hormone therapy selected from the group consisting of luteinizing hormone-releasing hormone (LHRH) agonists (also known as gonadotropin-releasing hormone (GnRH) agonists), LHRH antagonists (also known as GnRH antagonists), and abiraterone.

9. The method according to claim 1, wherein the pharmaceutically acceptable salt of masitinib is masitinib mesilate.

10. The method according to claim 1, wherein said masitinib, or the pharmaceutically acceptable salt or solvate thereof, is administered at a dose ranging from 1 to 12 mg/kg/day (mg per kilo body weight per day).

11. The method according to claim 1, wherein said masitinib, or the pharmaceutically acceptable salt or solvate thereof, is administered at a dose ranging from 3 to 6 mg/kg/day.

12. The method according to claim 1, wherein said masitinib, or the pharmaceutically acceptable salt or solvate thereof, is administered at a dose of 6 mg/kg/day.

13. The method according to claim 1, wherein said masitinib, or the pharmaceutically acceptable salt or solvate thereof, is administered orally.

14. The method according to claim 1, wherein said masitinib, or the pharmaceutically acceptable salt or solvate thereof, is administered in two daily intakes.

15. The method according to claim 1, wherein said masitinib, or the pharmaceutically acceptable salt or solvate thereof, is administered with at least one further pharmaceutically active agent.

16. The method according to claim 15, wherein said at least one further pharmaceutically active agent is selected from chemotherapeutic agents and corticoids.

* * * * *